(12) United States Patent
Andino et al.

(10) Patent No.: US 10,537,714 B2
(45) Date of Patent: Jan. 21, 2020

(54) STABILIZING DEVICE FOR AN EXTENSION SET

(75) Inventors: Rafael V. Andino, Grayson, GA (US); Christopher J. Brooks, Glen Cove, NY (US)

(73) Assignee: Venetec International, Inc., Murray Hill, NJ (US)

( * ) Notice: Subject to any disclaimer, the term of this patent is extended or adjusted under 35 U.S.C. 154(b) by 1933 days.

(21) Appl. No.: 13/500,853

(22) PCT Filed: Nov. 11, 2010

(86) PCT No.: PCT/US2010/056421
§ 371 (c)(1),
(2), (4) Date: Jul. 13, 2012

(87) PCT Pub. No.: WO2011/060197
PCT Pub. Date: May 19, 2011

(65) Prior Publication Data
US 2012/0271240 A1    Oct. 25, 2012

Related U.S. Application Data

(60) Provisional application No. 61/260,366, filed on Nov. 11, 2009.

(51) Int. Cl.
*A61M 25/02* (2006.01)

(52) U.S. Cl.
CPC .................................. *A61M 25/02* (2013.01)

(58) Field of Classification Search
CPC ............ A61M 2025/024; A61M 25/02; A61M 2025/0266; A61M 2025/028; A61M 2005/1416; A61M 2025/0246; A61M 2025/0253; A61B 2017/3492

USPC .................................. 604/180, 174, 164.04
See application file for complete search history.

(56) References Cited

U.S. PATENT DOCUMENTS

| 2,525,398 A | 10/1950 | Collins |
| 2,533,961 A | 12/1950 | Rousseau et al. |
| 2,707,953 A | 5/1955 | Ryan |
| 2,893,671 A | 7/1959 | Flora et al. |

(Continued)

FOREIGN PATENT DOCUMENTS

| CA | 995995 A1 | 8/1976 |
| CA | 2281457 A1 | 2/2001 |

(Continued)

OTHER PUBLICATIONS

International Search Report and Written Opinion dated Jan. 12, 2011 for International Application No. PCT/US 10/56421, filed Nov. 11, 1010.

(Continued)

*Primary Examiner* — Deanna K Hall
(74) *Attorney, Agent, or Firm* — Rutan & Tucker LLP

(57) ABSTRACT

A medical article, such as a connector fitting or extension set, is stabilized on a patient with a retainer and a dressing integrally attached to an anchor pad supporting the retainer. The connector fitting or extension set may be integrally formed with the retainer. The connector fitting or extension set may comprise a spin nut configured to secure to a catheter hub having a catheter connected thereto. One or more of the anchor pad, dressing, and catheter may comprise an antibacterial or antimicrobial agent.

15 Claims, 9 Drawing Sheets

(56) References Cited

U.S. PATENT DOCUMENTS

| | | |
|---|---|---|
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raaelli, Sr. |
| 3,529,597 A | 9/1970 | Fuzak |
| 3,602,227 A | 8/1971 | Andrew |
| 3,630,195 A | 12/1971 | Santomieri |
| 3,677,250 A | 7/1972 | Thomas |
| 3,766,915 A | 10/1973 | Rychlik |
| 3,834,380 A * | 9/1974 | Boyd .................. A61M 25/02 128/DIG. 26 |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,905,322 A | 9/1975 | Peterman et al. |
| 3,906,592 A | 9/1975 | Sakasegawa et al. |
| 3,906,946 A | 9/1975 | Nordstrom |
| 3,934,576 A | 1/1976 | Danielsson |
| 3,942,228 A | 3/1976 | Buckman et al. |
| 3,973,565 A | 8/1976 | Steer |
| 3,993,081 A | 11/1976 | Cussell |
| 4,020,835 A | 5/1977 | Nordstrom et al. |
| 4,030,540 A | 6/1977 | Roma |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |
| 4,193,174 A | 3/1980 | Stephens |
| 4,209,015 A | 6/1980 | Wicks |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,356,599 A | 11/1982 | Larson et al. |
| 4,362,156 A | 12/1982 | Feller, Jr. et al. |
| 4,392,853 A | 7/1983 | Muto |
| 4,397,647 A | 8/1983 | Gordon |
| 4,402,691 A | 9/1983 | Rosenthal et al. |
| 4,405,163 A | 9/1983 | Voges et al. |
| 4,405,312 A | 9/1983 | Gross et al. |
| 4,442,994 A | 4/1984 | Logsdon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,484,913 A | 11/1984 | Swauger |
| 4,498,903 A | 2/1985 | Mathew |
| 4,516,968 A | 5/1985 | Marshall et al. |
| 4,517,971 A | 5/1985 | Sorbonne |
| 4,563,177 A | 1/1986 | Kamen |
| 4,583,976 A | 4/1986 | Ferguson |
| 4,623,102 A | 11/1986 | Hough, Jr. |
| 4,633,863 A | 1/1987 | Filips et al. |
| 4,650,473 A | 3/1987 | Bartholomew et al. |
| 4,659,329 A | 4/1987 | Annis |
| 4,660,555 A | 4/1987 | Payton |
| 4,711,636 A | 12/1987 | Bierman |
| 4,726,716 A | 2/1988 | McGuire |
| 4,733,666 A | 3/1988 | Mercer, Jr. |
| 4,742,824 A | 5/1988 | Payton et al. |
| 4,762,513 A | 8/1988 | Choy et al. |
| 4,775,121 A | 10/1988 | Carty |
| 4,808,162 A | 2/1989 | Oliver |
| 4,823,789 A | 4/1989 | Beisang, III |
| 4,826,466 A | 5/1989 | Triquet |
| 4,826,486 A | 5/1989 | Palsrok et al. |
| 4,838,878 A | 6/1989 | Kalt et al. |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,981,475 A | 1/1991 | Haindl |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,084,026 A | 1/1992 | Shapiro |
| 5,098,399 A | 3/1992 | Tollini |
| 5,100,393 A | 3/1992 | Johnson |
| 5,112,313 A | 5/1992 | Sallee |
| 5,137,519 A | 8/1992 | Littrell et al. |
| 5,147,322 A | 9/1992 | Bowen et al. |
| 5,156,641 A | 10/1992 | White |
| 5,188,609 A | 2/1993 | Bayless et al. |
| 5,192,273 A | 3/1993 | Bierman et al. |
| 5,192,274 A | 3/1993 | Bierman |
| 5,195,981 A | 3/1993 | Johnson |
| 5,210,913 A | 5/1993 | Clark |
| 5,226,892 A | 7/1993 | Boswell |
| 5,234,185 A | 8/1993 | Hoffman et al. |
| 5,248,306 A | 9/1993 | Clark et al. |
| 5,263,943 A | 11/1993 | Vanderbrook |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,306,256 A | 4/1994 | Jose |
| 5,308,337 A | 5/1994 | Bingisser |
| 5,314,411 A | 5/1994 | Bierman et al. |
| 5,322,514 A | 6/1994 | Steube et al. |
| 5,330,438 A | 7/1994 | Gollobin et al. |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,368,575 A | 11/1994 | Chang |
| 5,380,293 A | 1/1995 | Grant |
| 5,380,294 A | 1/1995 | Persson |
| 5,380,301 A | 1/1995 | Prichard et al. |
| 5,382,240 A | 1/1995 | Lam |
| 5,389,082 A | 2/1995 | Baugues et al. |
| 5,395,344 A | 3/1995 | Beisang, III et al. |
| 5,398,679 A | 3/1995 | Freed |
| 5,403,285 A | 4/1995 | Roberts |
| 5,413,562 A | 5/1995 | Swauger |
| 5,382,239 A | 7/1995 | Orr et al. |
| 5,431,695 A | 7/1995 | Wiklund et al. |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |

(56) References Cited

U.S. PATENT DOCUMENTS

| | | |
|---|---|---|
| 5,484,420 A | 1/1996 | Russo |
| 5,494,245 A | 2/1996 | Suzuki et al. |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,549,567 A | 8/1996 | Wolman |
| D375,355 S | 11/1996 | Bierman |
| 5,578,013 A | 11/1996 | Bierman |
| 5,626,565 A | 5/1997 | Landis et al. |
| 5,632,274 A | 5/1997 | Quedens et al. |
| 5,637,098 A | 6/1997 | Bierman |
| 5,638,814 A | 6/1997 | Byrd |
| 5,643,217 A | 7/1997 | Dobkin |
| 5,672,159 A | 9/1997 | Warrick |
| 5,681,290 A | 10/1997 | Alexander |
| 5,685,859 A | 11/1997 | Kornerup |
| 5,686,096 A * | 11/1997 | Khan ............... A61M 25/02 424/443 |
| 5,690,617 A | 11/1997 | Wright |
| 5,693,032 A | 12/1997 | Bierman |
| 5,697,907 A | 12/1997 | Gaba |
| 5,702,371 A | 12/1997 | Bierman |
| D389,911 S | 1/1998 | Bierman |
| 5,709,665 A | 1/1998 | Vergano et al. |
| 5,722,959 A | 3/1998 | Bierman |
| 5,738,660 A | 4/1998 | Luther |
| 5,755,225 A | 5/1998 | Hutson |
| 5,795,335 A | 8/1998 | Zinreich |
| 5,800,402 A | 9/1998 | Bierman |
| 5,810,781 A | 9/1998 | Bierman |
| 5,810,835 A * | 9/1998 | Ryan ............... A61M 25/0084 604/159 |
| 5,827,230 A * | 10/1998 | Bierman ............... A61M 25/02 604/174 |
| 5,827,239 A | 10/1998 | Dillon et al. |
| 5,833,667 A | 11/1998 | Bierman |
| 5,846,255 A | 12/1998 | Casey |
| 5,916,199 A | 6/1999 | Miles |
| 5,944,696 A | 8/1999 | Bayless et al. |
| 5,989,213 A | 11/1999 | Maginot |
| 6,001,081 A | 12/1999 | Collen |
| 6,015,119 A | 1/2000 | Starchevich |
| 6,027,480 A | 2/2000 | Davis et al. |
| 6,074,368 A | 6/2000 | Wright |
| 6,113,577 A | 9/2000 | Hakky et al. |
| 6,132,398 A | 10/2000 | Bierman |
| 6,139,532 A | 10/2000 | Howell et al. |
| 6,206,897 B1 | 3/2001 | Jamiolkowski et al. |
| 6,213,979 B1 | 4/2001 | Bierman |
| 6,224,571 B1 | 5/2001 | Bierman |
| 6,228,064 B1 | 5/2001 | Abita et al. |
| 6,231,548 B1 | 5/2001 | Bassett |
| 6,273,873 B1 * | 8/2001 | Fleischer ............... A61M 25/02 604/1 |
| 6,283,945 B1 | 9/2001 | Bierman |
| 6,290,265 B1 | 9/2001 | Warburton-Pitt et al. |
| 6,290,676 B1 | 9/2001 | Bierman |
| 6,311,933 B1 | 11/2001 | Starchevich |
| 6,332,874 B1 | 12/2001 | Eliasen et al. |
| 6,361,523 B1 | 3/2002 | Bierman |
| 6,387,075 B1 | 5/2002 | Stivland et al. |
| 6,387,076 B1 | 5/2002 | Landuyt |
| 6,413,240 B1 | 7/2002 | Bierman et al. |
| 6,428,513 B1 | 8/2002 | Abrahamson |
| 6,428,514 B1 | 8/2002 | Goebel et al. |
| 6,428,516 B1 | 8/2002 | Bierman |
| 6,447,485 B2 | 9/2002 | Bierman |
| 6,447,486 B1 | 9/2002 | Tollini |
| 6,458,104 B2 | 10/2002 | Gautsche |
| 6,482,183 B1 | 11/2002 | Pausch et al. |
| 6,488,664 B1 | 12/2002 | Solomon et al. |
| 6,491,713 B1 | 12/2002 | Deininger et al. |
| 6,500,154 B1 | 12/2002 | Hakky et al. |
| 6,572,587 B2 | 6/2003 | Lehrman et al. |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,631,715 B2 | 10/2003 | Kirn |
| 6,663,600 B2 | 12/2003 | Bierman et al. |
| 6,786,892 B2 | 9/2004 | Bierman |
| 6,824,527 B2 | 11/2004 | Gollobin |
| 6,837,875 B1 | 1/2005 | Bierman |
| 6,841,715 B2 | 1/2005 | Roberts |
| 6,872,194 B2 | 3/2005 | Doyle et al. |
| 6,929,625 B2 | 8/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,984,145 B1 | 1/2006 | Lim |
| 7,018,362 B2 | 3/2006 | Bierman et al. |
| 7,137,968 B1 * | 11/2006 | Burrell et al. ............... 604/180 |
| D533,442 S | 12/2006 | Baylor |
| 7,175,615 B2 | 2/2007 | Hanly et al. |
| 7,247,150 B2 | 7/2007 | Bierman |
| 7,294,752 B1 | 11/2007 | Propp |
| D593,680 S | 6/2009 | Hafele et al. |
| 7,563,251 B2 | 7/2009 | Bierman et al. |
| 7,704,260 B2 | 4/2010 | Skakoon et al. |
| 7,776,003 B2 | 8/2010 | Zauner |
| 7,785,295 B2 | 8/2010 | Bierman |
| 8,016,792 B2 | 9/2011 | Wright et al. |
| 8,366,678 B2 | 2/2013 | Bierman et al. |
| 8,419,689 B2 * | 4/2013 | Fink ............... A61M 25/02 206/363 |
| 8,728,039 B2 | 5/2014 | Bierman et al. |
| 9,138,560 B2 | 9/2015 | Wright et al. |
| 9,468,740 B2 | 10/2016 | Bierman et al. |
| 9,480,821 B2 | 11/2016 | Ciccone et al. |
| 9,974,929 B2 | 5/2018 | Ciccone et al. |
| 2002/0068904 A1 | 6/2002 | Bierman et al. |
| 2002/0165493 A1 | 11/2002 | Bierman |
| 2003/0229313 A1 | 12/2003 | Bierman |
| 2004/0034330 A1 | 2/2004 | Bierman et al. |
| 2005/0096606 A1 | 5/2005 | Millerd |
| 2005/0113759 A1 | 5/2005 | Mueller et al. |
| 2005/0192539 A1 | 9/2005 | Bierman et al. |
| 2005/0197628 A1 | 9/2005 | Roberts et al. |
| 2006/0089600 A1 | 4/2006 | Bierman et al. |
| 2006/0129103 A1 | 6/2006 | Bierman et al. |
| 2006/0135944 A1 | 6/2006 | Bierman |
| 2007/0043326 A1 | 2/2007 | Navarro et al. |
| 2007/0142782 A2 | 6/2007 | Bierman |
| 2007/0219500 A1 | 9/2007 | Wright et al. |
| 2007/0276335 A1 | 11/2007 | Bierman |
| 2008/0132848 A1 | 6/2008 | Wright et al. |
| 2008/0200880 A1 | 8/2008 | Kyvik et al. |
| 2009/0143740 A1 | 6/2009 | Bierman et al. |
| 2009/0143741 A1 | 6/2009 | Burn |
| 2009/0209906 A1 | 8/2009 | Tanaka et al. |
| 2010/0100049 A1 * | 4/2010 | Godfrey ............... A61M 25/02 604/180 |
| 2010/0324491 A1 | 12/2010 | Bierman et al. |
| 2012/0123343 A1 * | 5/2012 | Aviles ............... 604/180 |
| 2012/0136314 A1 | 5/2012 | Ciccone et al. |
| 2012/0143140 A1 | 6/2012 | Bierman et al. |
| 2012/0271240 A1 | 10/2012 | Andino et al. |
| 2014/0343501 A1 | 11/2014 | Bierman et al. |
| 2017/0043131 A1 | 2/2017 | Ciccone et al. |

FOREIGN PATENT DOCUMENTS

| | | |
|---|---|---|
| CA | 2483995 A1 | 4/2004 |
| DE | 2341297 A1 | 4/1975 |
| EP | 0064284 A2 | 11/1982 |
| EP | 0247590 A2 | 12/1987 |
| EP | 0356683 A1 | 3/1990 |
| EP | 0440101 A2 | 8/1991 |
| EP | 0 567 029 A1 | 10/1993 |
| EP | 0931560 A1 | 7/1999 |
| EP | 2968850 A1 | 1/2016 |

(56) References Cited

FOREIGN PATENT DOCUMENTS

| | | |
|---|---|---|
| EP | 2968850 B1 | 2/2019 |
| FR | 1184139 A | 7/1959 |
| FR | 2852520 A1 | 9/2004 |
| GB | 2063679 A | 6/1981 |
| GB | 2086466 A | 5/1982 |
| GB | 2288542 A | 10/1995 |
| GB | 2333234 A | 7/1999 |
| GB | 2344054 A | 5/2000 |
| JP | S60-051377 | 4/1985 |
| JP | 01308572 | 12/1989 |
| JP | H04-037448 | 3/1992 |
| JP | 1994-344852 A | 12/1994 |
| JP | 1995-028563 | 5/1995 |
| JP | H08-257138 A | 10/1996 |
| JP | 2005-535432 A | 11/2005 |
| JP | 04-051767 B2 | 2/2008 |
| JP | 2009-507533 A | 2/2009 |
| WO | 8001458 A1 | 7/1980 |
| WO | 8502774 A1 | 7/1985 |
| WO | 9116939 A1 | 11/1991 |
| WO | 9219309 A1 | 11/1992 |
| WO | 9610435 A1 | 4/1996 |
| WO | 1996/026756 A1 | 9/1996 |
| WO | 9853872 A1 | 12/1998 |
| WO | 9902399 A1 | 1/1999 |
| WO | 1999/020334 A1 | 4/1999 |
| WO | WO 99/55409 | 11/1999 |
| WO | 2001/068180 A1 | 9/2001 |
| WO | 2004016309 A2 | 2/2004 |
| WO | 2006/113620 A2 | 10/2006 |
| WO | 2007028007 A2 | 3/2007 |
| WO | 2008051810 A2 | 5/2008 |
| WO | 2011/060197 A1 | 5/2011 |

OTHER PUBLICATIONS

Extended European Search Report for EP 07 71 7867, PCT/US2007/000969, dated Oct. 14, 2010.
Medtronic. Intracranial Pressure Monitoring: A Handbook for the Nursing Professional. (2000).
Multiple-Lumen Central Venous Catheterization Product With Arrow+gard.™. Antiseptic Surface (Arrow International brochure) (Apr. 1994).
PCT/US07/00969 filed Jan. 11, 2007, International Search Report and Written Opinion, dated Sep. 25, 2007.
PCT/US07/00969 filed Nov. 1, 2007 International Search Report dated Sep. 25, 2007.
PCT/US07/00969 filed Nov. 1, 2007 Written Opinion dated Sep. 25, 2007.
PCT/US07/84346 filed Nov. 9, 2007 International Search Report and Written Opinion dated Oct. 31, 2008.
PCT/US08/68854 filed Jun. 30, 2008 International Search Report dated Sep. 5, 2008.
PCT/US08/68854 filed Jun. 30, 2008 Written Opinion dated Sep. 5, 2008.
PCT/US2001/006836 filed Feb. 3, 2001 International Search Report dated Aug. 2, 2001.
PCT/US2008/068854 filed Jun. 30, 2008 International Preliminary Report dated Sep. 5, 2008.
PCT/US2014/020207 filed Mar. 4, 2014 International Search Report and Written Opinion dated Jun. 12, 2014.
Photographs (4) of Catheter Clamp and Rigid Fastener sold by Arrow International. Inc.
Search Result, Percufix® Catheter Cuff Kit, downloaded from the Internet on Aug. 15, 2001.
U.S. Appl. No. 11/690,101 filed Mar. 22, 2007 Advisory Action dated Dec. 3, 2014.
U.S. Appl. No. 11/690,101 filed Mar. 22, 2007 Final Office Action dated Sep. 25, 2014.
U.S. Appl. No. 13/001,924 filed Jan. 30, 2012 Advisory Action dated Jun. 25, 2015.
U.S. Appl. No. 14/283,137 filed May 20, 2014 Non-Final Office Action dated Oct. 22, 2015.
EP 14770518.0 filed Sep. 7, 2015 Extended European Search Report, dated Aug. 23, 2016.
U.S. Appl. No. 14/859,090 filed Sep. 18, 2015 Notice of Allowance dated Sep. 27, 2016.
U.S. Appl. No. 14/283,137 filed May 20, 2014 Final Office Action dated Mar. 3, 2016.
U.S. Appl. No. 13/001,924 filed Jan. 30, 2012 Non-Final Office Action dated Mar. 28, 2016.
U.S. Appl. No. 14/283,137 filed May 20, 2014 Advisoary Action dated May 17, 2016.
U.S. Appl. No. 14/859,090 filed Sep. 18, 2015 Non-Final Office Action dated Apr. 7, 2016.
EP 14770518.0 filed Sep. 7, 2015 Office Action, dated Jul. 4, 2017.
U.S. Appl. No. 15/336,537 filed Oct. 27, 2016 Non-Final Office Action dated Jun. 9, 2017.
EP 14770518.0 filed Sep. 7, 2015 Office Action, dated Nov. 20, 2017.
JP 2016-500588 filed Sep. 11, 2015 Office Action dated Dec. 27, 2017.
U.S. Appl. No. 14/764,979 filed Jul. 30, 2015 Non-Final Office Action dated Feb. 7, 2018.
U.S. Appl. No. 15/336,537 filed Oct. 27, 2016 Final Office Action dated Nov. 14, 2017.
AU 2014237929 filed Jul. 9, 2015 Examination Report dated Feb. 9, 2018.
AU 2014237929 filed Jul. 9, 2015 Examination Report dated May 11, 2018.
CN 201480015384.2 filed Sep. 14, 2015 Office Action dated Feb. 5, 2018.
CN 201480015384.2 filed Sep. 14, 2015 Office Action dated Mar. 27, 2019.
CN 201480015384.2 filed Sep. 14, 2015 Office Action dated Oct. 31, 2018.
EP 14770518.0 filed Sep. 7, 2015 Intent to Grant, dated Sep. 27, 2018.
EP 14770518.0 filed Sep. 7, 2015 Office Action, dated Apr. 24, 2018.
EP07717867.1 filed Aug. 4, 2008 Office Action dated Aug. 21, 2018.
EP07717867.1 filed Aug. 4, 2008 Office Action dated May 17, 2019.
EP07717867.1 filed Aug. 4, 2008 Supplemental European Search Report dated Oct. 4, 2010.
JP 2016-500588 filed Sep. 11, 2015 Office Action dated Apr. 25, 2018.
U.S. Appl. No. 14/764,979 filed Jul. 30, 2015 Advisory Action dated May 14, 2019.
U.S. Appl. No. 14/764,979 filed Jul. 30, 2015 Advisory Action dated Nov. 15, 2018.
U.S. Appl. No. 14/764,979 filed Jul. 30, 2015 Final Office Action dated Apr. 4, 2019.
U.S. Appl. No. 14/764,979 filed Jul. 30, 2015 Final Office Action dated Aug. 8, 2018.
U.S. Appl. No. 14/764,979 filed Jul. 30, 2015 Non-Final Office Action dated Jan. 11, 2019.
U.S. Appl. No. 14/764,979 filed Jul. 30, 2015 Non-Final Office Action dated Jun. 28, 2019.

* cited by examiner

STABILIZING DEVICE FOR AN EXTENSION SET

CROSS-REFERENCE TO RELATED APPLICATIONS

This application is the National Stage of International Application No. PCT/US2010/056421, filed on Nov. 11, 2010, entitled "STABILIZING DEVICE FOR AN EXTENSION SET," which claims priority under 35 U.S.C. § 119(e) to U.S. Provisional Application No. 61/260,366, filed Nov. 11, 2009, entitled "STABILIZING DEVICE FOR AN EXTENSION SET," both of which are hereby incorporated by reference in their entirety.

BACKGROUND

Field of the Invention

The present invention relates generally to techniques, systems, and devices for stabilizing a catheter or catheter extension set or other medical article on a patient.

Description of the Related Art

Medical patients are often in need of repetitious administering of fluids or medications, or repetitious draining of fluids. It is very common in the medical industry to utilize medical tubing to provide various liquids or solutions to a patient. For example, medical tubing such as a catheter is often used to introduce fluids and medications directly into the patient or to withdraw fluids from the patient. In many cases, the catheter remains in place for many days. In some instances, a catheter may be attached to a patient for an even lengthier period of time, and may require minimal movement for proper functioning.

It is often advantageous to restrict the movement of the catheter. A moving catheter may cause discomfort to the patient, restrict the administering of fluids or medications or the draining of fluids, cause infection, or become dislodged from the patient unintentionally. In order to keep the catheter or other medical tubing properly positioned for the duration of treatment, the catheter or medical tubing can be stabilized on the patient in a variety of ways. Most commonly, the medical provider may attempt to restrict movement of the catheter by securing the distal end of the catheter, or a portion of a medical device connected to the catheter such as a connector fitting, to the patient using tape. Medical providers commonly place long pieces of tape across the distal end of the catheter, often in a crisscross pattern, to secure the catheter distal end to the patient. This securement is intended to inhibit disconnection between the catheter and the patient or between the catheter and another medical article, such as a drainage tube, as well as to prevent the catheter from catching on other objects, such as on a bed rail.

Stabilizing a catheter with tape upon the patient, however, has certain drawbacks. For example, taped connections often collect contaminants and dirt. This potentially can lead to infection of the patient, particularly at an insertion site where the catheter is inserted into the patient. Taped stabilization typically leaves the insertion site exposed to these contaminants and dirt and other foreign objects that may be harmful to the patient and/or compromise the stabilization of the catheter. Gathering or collecting of contaminants by the tape may exacerbate any problems at the insertion site. Normal protocol therefore requires periodic tape changes in order to inhibit germ growth. Such periodic changes, however, often disrupt any attempts or mechanisms used to shield or protect the insertion site, and may compel detrimental manipulation of the areas around the insertion site.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide several advantages over other securement devices.

One aspect of the present invention includes a stabilization system. The stabilization system includes an anchor pad, a retainer supported by the anchor pad and configured to receive at least a portion of a medical article, and a dressing secured to the anchor pad so as to move between an open position and a closed position. At least a portion of a surface of the anchor pad is covered by an adhesive for attachment to a patient's skin.

Another aspect of the present invention also includes a stabilization system. The stabilization system includes an anchor pad, a connector fitting supported by the anchor pad and having a spin nut, and a dressing secured to the anchor pad so as to move between an open position and a closed position. At least a portion of a surface of the anchor pad is covered by an adhesive for attachment to a patient's skin. The spin nut may be configured to secure to a catheter hub.

Yet another aspect of the present invention also includes a stabilization system. The stabilization system includes an anchor pad, an extension set supported by the anchor pad and having a spin nut, and a dressing secured to the anchor pad so as to move between an open position and a closed position. At least a portion of a surface of the anchor pad is covered by an adhesive for attachment to a patient's skin. The spin nut may be configured to secure to a catheter hub.

BRIEF DESCRIPTION OF THE DRAWINGS

The above mentioned and other features of the invention will now be described with reference to the drawings of several embodiments of the present stabilization system. The illustrated embodiments of the stabilization system are intended to illustrate, but not to limit the invention. The drawings contain the following figures.

DETAILED DESCRIPTION OF CERTAIN EMBODIMENTS

Figure 1:
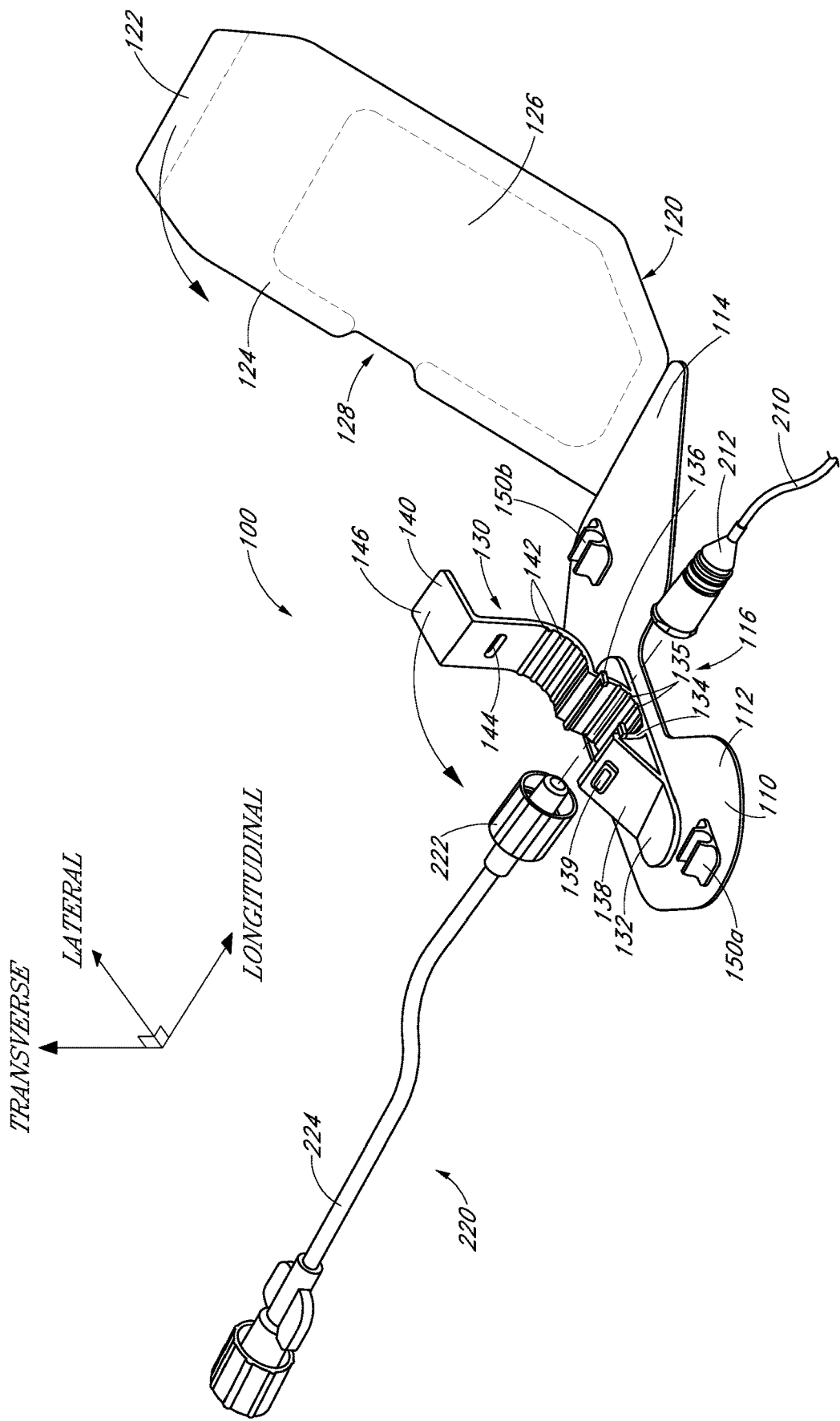
FIG. 1 is a perspective view of an embodiment of a stabilization system and dressing.

The following description and examples illustrate preferred embodiments of the present stabilization system disclosed in the context of use with exemplary catheters and catheter extension sets. More specifically, the embodiments relate to a stabilization system and related techniques that stabilize a medical article in position upon a patient. The embodiments of the stabilization system are illustrated with a catheter extension set having a male luer-lock connection fitting. The principles of the present invention, however, are not limited to extension sets or fittings such as those shown. It will be understood by those of skill in the art in view of the present disclosure that the securement system described can be used with other types of medical articles, including, but not limited to catheters and catheter hubs of various design, either with or without connectors or extension sets, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes, any other sort of fluid supply or medical lines, connector fittings, and scopes, as well as electrical wires or cables connected to external or implanted electronic devices or sensors. The medical articles can be a single medical article or a combination of medical articles.

One skilled in the art may also find additional applications for the devices and systems disclosed herein. Accordingly, the illustration and description of the stabilization system in connection with a catheter and catheter extension set is merely exemplary of one possible application of the stabilization system and technique disclosed. For ease of description, the term extension set or catheter extension set is used herein to generically refer to the above listed medical articles, for example but without limitation, and should not be construed in a limited manner.

The securement system described herein is especially adapted to arrest at least transverse movement of an extension set and attached catheter, as well as hold these medical articles against the patient, and to protect an area in proximity to an insertion site. The securement system accomplishes this without meaningfully impairing (i.e., substantially occluding) fluid flow through a lumen of the medical article or impairing insertion of the medical article. In some embodiments, retention mechanisms to accomplish this include a channel that is securable about a medical article and integrated with a dressing. In other embodiments, retention mechanisms to accomplish this include a retention mechanism having an integral hub or connector fitting and an integrated dressing.

Some embodiments of the stabilization system releasably engage a catheter extension set or other medical article attached thereto. This allows the extension set to be disconnected from the stabilization system, and from the patient, for any of a variety of known purposes. For instance, the medical provider may want to remove the extension set to clean or replace the extension set or to clean an area surrounding where the extension set is located on the patient. The disengagement of the extension set from the stabilization system, however, can be accomplished without removing an anchor pad from the patient. Thus, the medical provider may move the extension set without irritating the skin of the patient or disrupting a catheter inserted in the skin of the patient.

With reference now to FIG. 1, an embodiment of a stabilization system 100 includes an anchor pad 110, a dressing 120, a retainer 130, and tube clips 150a and 150b. Also shown in FIG. 1 are a catheter 210 attached to a catheter hub 212 and a catheter extension set 220. The anchor pad 110 is configured to be secured to a patient's skin. The retainer 130 and tube clips 150a and 150b are attached to an upper surface of the anchor pad 110. The retainer 130 is configured to engage a medical article, for example the catheter extension set 220, as will be described in additional detail below.

To assist in the description of the components of embodiments of the stabilization system, the following coordinate terms are used, consistent with the coordinate axes illustrated in FIG. 1. A "longitudinal axis" is generally parallel to a channel formed by the retainer 130. A "lateral axis" is normal to the longitudinal axis and is generally parallel to the plane of the anchor pad 110. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body, as will be understood by one of skill in the art.

As can be seen in FIG. 1, the anchor pad 110 is generally crescent shaped with a rounded end 112 and a pointed end 114 extending farther than the rounded end. This pointed end 114 forms an extended portion for engagement with the dressing 120, as will be described in additional detail below. An indented region 116 of the anchor pad 120, which forms the proximal curve of the crescent shape, defines an insertion site area for insertion of a catheter stabilized by the stabilization system 100. However, other shapes and configurations of the anchor pad 110 are possible and within the scope of this description. For example, the end 112 may be shaped such that it is not rounded, and the end 114 may be shaped such that it is not pointed. As another example, the end 112 may extend as far as or farther than the end 114.

In the illustrated embodiment, the anchor pad 110 is configured for placement on a distal surface of a patient's hand. The anchor pad 110, however, may be larger or smaller, and may be shaped for placement on a different area of the patient's body. The anchor pad 110 may be any size or shape that allows attachment of the anchor pad 110 to a patient's skin and that is configured to support at least the retainer 130. In the illustrated embodiment, the anchor pad 110 is also configured to support the tube clips 150a and 150b. In other embodiments, one or both of the tube clips 150a and 150b are omitted. In some embodiments, the anchor pad 110 is configured to support more than two tube clips. In some embodiments, one or both of the tube clips 150a and 150b are supported by a separate, auxiliary anchor pad or pads.

The anchor pad 110 has a lower adhesive surface (not shown) which may adhere to the skin of a patient and an upper layer. The upper layer is configured to support at least the retainer 130, as described above. In combination, the lower adhesive surface, upper layer, and possibly one or more intermediate layers may comprise a laminate structure. A suitable laminate that comprises a foam or woven material with an adhesive layer is available commercially from Avery Dennison of Painsville, Ohio. The anchor pad 110 may be configured as a flexible structure configured to conform to the surface of a patient's skin.

The lower adhesive surface or layer may be a medical-grade adhesive and can be either diaphoretic or nondiaphoretic, depending upon the particular application. The lower adhesive surface may have additional types of medical adhesives laminated thereto. In some embodiments, the lower adhesive layer comprises an anti-bacterial or anti-microbial material. For example, the lower adhesive layer may comprise one or more oligodynamic metal salts or oxides, or a combination of salts and oxides. In some embodiments, the lower adhesive layer comprises a silver material, for example a silver salt, colloid, or complex. The adhesive surface may be a solid layer or may be configured as an intermittent layer such as in a pattern of spots or strips.

The lower adhesive surface can be applied to the anchor pad 110 during manufacture, and may be further covered with a release liner (not shown), described below. Alternatively, it is possible to apply a double-sided adhesive tape to the upper layer before application.

The upper layer may comprise a foam (e.g., closed-cell polyethylene foam) or woven material (e.g., tricot) layer. A surface of the foam or woven material layer constitutes the upper layer of the anchor pad 110. In the alternative, the upper layer may comprise an upper paper or other nonwoven cloth layer, and an inner foam layer may be placed between the upper layer and lower adhesive surface.

A removable release liner may cover the lower adhesive surface before use. The release liner may resist tearing and be divided into a plurality of pieces to assist removal of the release liner and ease attachment of the anchor pad 110 to a patient's skin. The release liner may be divided into two adjacent pieces. The liner may be made of a paper, plastic, polyester, or similar material. For example, the release liner may comprise a material made of polycoated, siliconized paper, or another suitable material such as high density polyethylene, polypropylene, polyolefin, or silicon coated paper.

With reference now to the dressing 120, it can be seen in FIG. 1 that the dressing 120 is attached to and/or integrated with the anchor pad 110. The dressing 120 is configured to fold, bend, or rotate down over the insertion site area defined by the indented region 116 of the anchor pad 110. A proximal extended portion of the anchor pad 110, illustrated in FIG. 1 as the pointed end 114, provides an attachment area to attach or integrate the dressing 120 with the anchor pad 110. Additionally, the extended portion may longitudinally offset the dressing 120 from a location where the retainer 130 is supported by the anchor pad 110 such that when the dressing 120 is folded down over the insertion site, the anchor pad 110 will not substantially cover or obstruct a catheter hub stabilized by the stabilization system 100 or the retainer 130 itself.

The dressing 120 and the anchor pad 110 may be formed as an integral, single piece. Alternatively, the dressing 120 and the anchor pad 110 may be formed separately and then attached together. In this case, the dressing 120 and the anchor pad 110 may be attached by any means or mechanism that allows the dressing 120 to fold, bend, or rotate down over the insertion site area. Attachment means include glue or adhesive, a weld of the materials, heat sealing, mechanical fasteners such as staples or eyelets, or other such means of attachment. The pointed end 114 of the anchor pad 110 may be configured in any shape and size that allows attachment or integration of the dressing 120 with the anchor pad 110. The dressing 120 may be attached to an upper surface of the anchor pad 110, for example within an outer circumference of the anchor pad 110. In the illustrated embodiment, the dressing 120 is secured to an edge of the anchor pad 110 that is generally parallel to a longitudinal axis. The dressing 120, however, may be attached to or integrated with the anchor pad 110 such that the dressing 120 is skewed with respect to a longitudinal and/or a lateral axis.

In some embodiments, the anchor pad 110, the dressing 120, and/or the attachment means described above are configured to allow selective disconnection of the dressing 120 from the anchor pad 110. For example, when the anchor pad 110 and the dressing 120 are integrally formed, the region in which the dressing pad 120 folds may be scoured such that a medical provider may tear the dressing 120 away from the anchor pad 110. Of course, other means of removal or release may be employed to allow the dressing 120 to be disconnected from the anchor pad 110.

A release liner 122 may cover an adhesive surface 124 of the dressing 120 and may also cover an occlusive layer 126 of the dressing 120, as shown in FIG. 1. The adhesive surface 124 is configured to adhere to the skin of a patient and/or to portions of the upper layer of the anchor pad 110. The release liner 122 may cover the entire surface of the dressing 120, as illustrated, or may only cover adhesive portions of the dressing 120. As illustrated in FIG. 1, the release liner 122 includes a tab that extends beyond the edge of the dressing 120 to allow a medical provider to easily grip the release liner and remove it from the dressing 120. The tab may be located at any edge of the dressing 120, or a tab that projects out from the release liner 122 may be located within an area defined by the edges of the dressing 120. The release liner 122 may include an anti-microbial or anti-bacterial material or coating, and/or have silver particles dispersed throughout. The dressing 120 and release liner 122 may be prepared such that the release liner 122 maintains a covered surface of the occlusive layer 126 in a sterilized state. The release liner 122 may be configured similar to the release liner covering the lower adhesive surface of the anchor pad 110, described above.

In the illustrated embodiment, the adhesive surface 124 is formed in a ring shape on the periphery of the occlusive layer 126. This ring configuration will encircle the insertion site area when the adhesive layer 124 is adhered to the skin of the patient, but will not adhere to the point of insertion. Advantageously, this will reduce the likelihood of aggravating or excoriating the insertion site or skin around the insertion site, and will reduce the likelihood of introducing contaminants near or into the point of insertion. In addition, the adhesive surface 124 will not contact the catheter 210 or catheter hub 212 when the adhesive surface 124 is adhered to the skin. The ring is broken at a notch or indent 128 in the occlusive layer 126 to allow the catheter 210 and catheter hub 212 to be covered without being contacted by the adhesive surface 124. Thus, the adhesive surface will not adhere or stick to the catheter 210 or the catheter hub 212. In this way, sticky residues and buildup on the catheter 210 and catheter hub 212 may be reduced or avoided.

The adhesive surface 124 may instead cover all or a majority of the occlusive layer 126. Such configuration will increase the contact area of the adhesive surface 124 with the skin of the patient and with portions of the anchor pad 110, and may result in a more secure attachment of the dressing 120 to the patient. The adhesive surface 124 may be configured similar to the lower adhesive surface of the anchor pad 110, described above.

The occlusive layer 126 is configured to be waterproof or otherwise impermeable to liquids and in some embodiments also restricts the flow of air. In other embodiments, the occlusive layer 126 may be configured to be breathable, allowing air and/or moisture near an insertion site through to the other side of the occlusive layer 126 and away from the insertion site, while keeping at least external moisture on the other side of the occlusive layer 126 away from the insertion site. In some embodiments, the occlusive layer 126 is impermeable to viruses and bacteria, and may comprise or be coated with an anti-bacterial or anti-microbial material. In some embodiments, the occlusive layer 126 comprises or is coated with a waxy material. In some embodiments, the occlusive layer 126 comprises a film which may or may not be transparent. Selection of a transparent film for use as the occlusive layer 126 may allow a medical provider to see the insertion site and any administered catheter. In some embodiments, the occlusive layer 126 is absorbent. In some embodiments, the occlusive layer 126 comprises an absorbent acrylic, an alginate, a foam, a hydrocolloid, and/or a hydrogel material, and/or may comprise a silver material, for example a silver salt, colloid, or complex. In one embodiment, one or more oligodynamic metal salts or oxides, or a combination of salts and oxides are used in or on the occlusive layer 126 as an antimicrobial agent. In some embodiments, the occlusive layer 126 is configured similar to the upper layer of the anchor pad 110.

As described above, the occlusive layer 126 comprises a notch or indentation 128. This notch may reduce stress on the dressing 120 when the dressing is applied over a catheter and/or catheter hub. The dressing 120 may be configured to provide a waterproof seal around an insertion site when applied to the skin of a patient over a catheter and/or catheter hub. In some embodiments, the dressing 120 is still breathable while the waterproof seal is created.

In some embodiments, the dressing 120 comprises a hemostatic dressing. In such embodiments, securing the dressing 120 over an insertion site or other wound may inhibit blood from flowing from the site. For example, the dressing 120 may comprise or be coated with a hemostatic or antihemorrhagic agent such as chitosan or other polysaccharide, a collagen like microfibrillar hemostat, anhydrous aluminum sulfate, potassium alum, titanium dioxide, a gelatin, or a solution of thrombin.

With reference now to the retainer 130, it can be seen in FIG. 1 that the retainer 130 comprises a base 132, an open channel 134, a strap 140, and an angled support 138. The base 132 is attached to and supported by the anchor pad 110, and is configured to support the retainer 130 on the anchor pad 110 such that the retainer 130 does not rock or otherwise pivot on the anchor pad 110. Although the base 132 is shown as having an oblong shape with rounded ends, the base 132 may be shaped in any of a multitude of ways. In some embodiments, the retainer 130 is permanently adhered or affixed to the anchor pad 110.

The open channel 134 has a curvilinear shape configured to accept at least a portion of a medical article. In the illustrated embodiment, the open channel 134 is configured to accept a spin nut 222 of the catheter extension set 220 and thus the shape of the channel 134 approximates at least a portion of the spin nut 222. The channel 134 is shown as having an approximately semi-circular shape, but may be formed as having a different shape. In the illustrated embodiment, the width of the channel 134 in the lateral direction is consistent, but the channel 134 may vary in width. For example, the channel 134 may be formed in a tapering shape. The channel 134 may of course be configured to accept other medical articles.

In the illustrated embodiment, ribs 135 are disposed on an inner surface of the channel 134. The ribs may provide additional frictional surface for contacting the spin nut 222 and inhibiting rotation of the spin nut 222 when at least a portion of the spin nut 222 is placed within the channel 134. In some embodiments, the ribs 135 are configured to complement or engage with longitudinal ribs, protrusions, or indentations on the spin nut 222. This interaction will further limit rotational motion of the spin nut 222 within the channel 134.

One or more of the ribs 135 may include a detent 136, as shown in FIG. 1. This detent extends towards the inside of the channel 134 and is configured to abut the spin nut 222 or other medical article being placed within the channel 134. When the spin nut 222 contacts the detent 136, the spin nut 222 will be inhibited from moving in at least one longitudinal direction. In some embodiments, the detent 136 is configured to interact with an indentation, groove, notch, or other feature on the spin nut. In the illustrated embodiments, two detents 136 are shown as being formed at the proximal ends of the uppermost ribs 135 of the channel 134. In other embodiments, fewer detents may be formed or a greater number of detents may be formed, for example on other ones of the ribs 135. In some embodiments, one or more detents are formed at the distal end of the channel 134. Placing a spin nut 222 between a detent formed at the proximal end of the channel 134 and a detent formed at the distal end of the channel 134 may inhibit longitudinal motion of the spin nut 222 in both longitudinal directions. The detents 136 may be formed in locations that are not aligned with the ribs 135. Further, the detents 136 may be formed at irregular locations about the channel 134, and need not be symmetric.

A strap 140 is attached to the open channel 134. The strap 140 is configured to close over the open channel 134 to form an enclosed area. When a portion of a medical article is placed inside the channel 134, the strap 140 can be moved over the medical article to encircle the medical article and retain or stabilize the medical article within the retainer 130. The strap 140 may be integral to the open channel 134, or may be attached thereto. In one embodiment, the strap 140 is integral to the open channel 134 and attached by a living hinge. In another embodiment, the strap 140 is formed separate from the channel 134 and attached thereto, for example by sonic welding. A multitude of attachment means may be used to attach the strap 140 to the channel 134 such that the strap 140 may be closed over the channel 134.

In one embodiment, the strap 140 comprises an elastomeric material. In this embodiment, the strap may be stretched or deformed slightly when closing about a medical article placed in the channel 134. Such elastic deformation may increase the stability with which the medical article is secured in the channel 134. In addition, the elastomeric material may have an increased frictional coefficient with the medical article as compared to certain other materials like hard plastics. As shown in the illustrated embodiment, the strap 140 may also have ribs 142 or other protrusions formed on an inside surface thereof. The ribs 142 on the strap 140 may be configured similar to the ribs 135 on the channel 134.

In the illustrated embodiment, the strap 140 is configured to retain the spin nut 222. Thus, the strap 140 is sized and shaped such that it can be placed over the portion of the spin nut 222 that is exposed after the spin nut 222 has been placed in the channel 134. When the strap 140 is formed of an elastomeric material, as described above, the strap 140 may conform to the shape of the spin nut 222 or other retained medical article when pulled over the spin nut 222. In the illustrated embodiment, the strap 140 is preformed in a shape that approximates at least an upper portion of the spin nut 222. When the strap 140 is closed over the spin nut 222 while the spin nut 222 is resting in the channel 134, the inner surfaces of the strap 140 and the channel 134 will lie in contact or close proximity to an outer surface of the spin nut 222.

In the illustrated embodiment, the strap 140 is formed with a hole 144 therethrough. The hole 144 is configured to accept a retention mechanism 139. The retention mechanism 139 is disposed on the angled support 138 in the illustrated embodiment. The angled support 138 holds the retention mechanism in a position such that it can engage with the strap 140. The angled support 138 may also serve to support, strengthen, or stabilize a portion of the channel 134. In some embodiments, the angled support 138 is omitted. In this case, the retention mechanism 139 may be disposed on an outer surface of the channel 134 or on the base 132. In some embodiments, an angled support is included on an opposite side of the channel 134 than shown.

In FIG. 1, the retention mechanism 139 is illustrated as being a protrusion that can be inserted through hole 144 to retain the strap 140 in a closed position over the channel 134. The retention mechanism 139 may comprise a lip to overhang a portion of the strap 140 after the retention mechanism 139 has been inserted through the hole 144. Other securing means may be used in place of the illustrated retention mechanism 139. For example, the strap 144 may be secured about a medical article by a snap, adhesive, hook and loop fasteners, or other securing means.

A length of the strap 140 is angled away from the portion of the strap 140 having the hole 144 to form a tab 146. The tab 146 may allow a medical provider to easily grip the strap 140 and disengage the strap 140 from the retention mechanism 139. In some embodiments, the tab 146 is omitted.

The retainer 130 may be constructed as a single piece or from a plurality of different pieces. For example, the entire retainer 130 may be formed by injection molding, or the channel 134 and the base 132 may be formed separately and thereafter joined together. The retainer 130 or portions thereof may be rigid or flexible. Suitable materials may include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. In one embodiment, the retainer 130 is formed by injection molding using a polyethylene or a polypropylene material or nylon. However, other materials can be utilized.

As can be seen in FIG. 1, the tube clips 150a and 150b each define a channel having a generally circular cross-sectional configuration truncated to form an opening. The diameter of the channel is desirably slightly less than that of a medical line, such as tube 224, to be secured in the tube clip 150a or 150b so as to ensure a secure interconnection. The channel receives a portion of the medical line through the opening upon application of gentle pressure or by pulling the line across and through the opening of the tube clip 150a or 150b. The clip 150a or 150b thereafter surrounds a portion of the line. The sides of the channel may be angled in relation to themselves or in relation to each other to accommodate a different medical line or other medical article.

The upper edge of the channel may include tapered ends at the proximal and distal ends of the clip 150a or 150b. Each tapered end may form a smooth transition between the side edge of the channel and the upper edge, and may taper in lateral width from the side edge toward the center of the tube clip 150a or 150b. The tapered ends help guide the medical line into the channel when a medical provider pulls the tube across the clip 150a or 150b. Thus, the medical provider does not have to pinch the line to insert it into the clip 150a or 150b. Also, the medical provider's gloves do not get stuck in the clip 150a or 150b when inserting the line, as is typically the case where the medical provider is required to pinch the line to insert it into the clip 150a or 150b.

In the illustrated embodiments, the tube clips 150a and 150b are disposed to either lateral side of the retainer 130. In some embodiments, one or both of the tube clips 150a and 150b are omitted. In some embodiments, additional tube clips may be disposed on the anchor pad 110. For example, a tube clip may be placed distal of the retainer 130 on the anchor pad 110. The tube clips 150a and 150b may be made of materials similar to those discussed above with respect to the retainer 130.

In some embodiments, the catheter 210 or a portion thereof comprises or is coated with an antimicrobial agent and/or an antibacterial agent. The antimicrobial agent may comprise a silver material, for example a silver salt, colloid, or complex. In one embodiment, one or more oligodynamic metal salts, oxides, or combination of salts and oxides are used.

The extension set 220 illustrated in FIG. 1 includes the spin nut 222 connected to the tube 224. Another spin nut may be connected to the tube 224 at the opposite end of the tube 224. In the illustrated embodiment, the extension set 220 includes a male luer-lock connection fitting at each side. In one embodiment, the catheter hub 212 comprises an integral one-way valve. Catheter extension sets are generally known to those skilled in the art.

Figure 2:
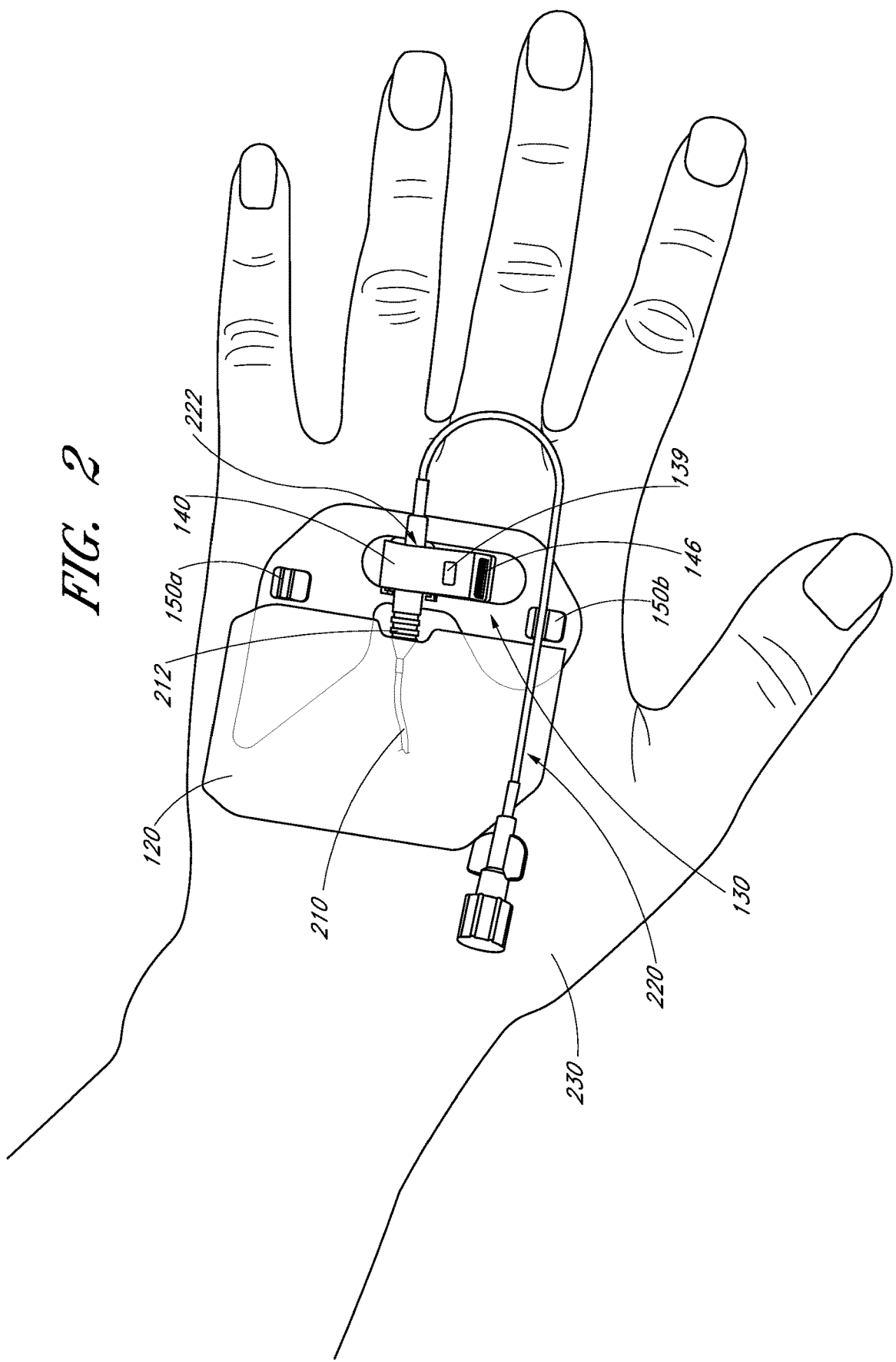
FIG. 2 is a top view of the stabilization system of FIG. 1 secured to a patient with the dressing folded against the patient.

FIG. 2 illustrates the stabilization system 100 secured to a hand 230 of a patient. Those of skill in the art, however, will recognize that the stabilization system 100 may instead be secured to other portions of a patient's body. In the embodiment illustrated in FIG. 2, the stabilization system 100 is illustrated in mirror image to the configuration shown in FIG. 1. Those of skill in the art will understand that the relative positioning of various elements of the stabilizing system 100 thus may be altered without compromising the advantages provided by the stabilizing system 100.

After the catheter 210 is inserted into the hand 230 and the hub 212 connected to the extension set 220 by using the spin nut 222, the spin nut 222 is placed in the channel 134 of the retainer 130. The anchor pad 110 may have already been adhered to the hand 230, or the anchor pad may thereafter be adhered to the hand 230. During this time, the dressing 120 is held away from the catheter 210 and the insertion site. The positioning of the dressing 120 may be maintained by a medical provider, or the dressing 120 or the area of attachment of the dressing 120 to the anchor pad 110 may be configured so as to bias the dressing 120 in this position.

The strap 140 is then pulled over the spin nut 222 until the hole 144 engages the retention mechanism 139. The retention mechanism 139 will maintain the strap 140 in a closed position over the spin nut 222. At this time, the release liner 122 of the dressing is removed to expose the adhesive surface 124. The dressing 120 is folded down over the insertion site and adhered to the skin of the patient, as shown in FIG. 2. Of course, the dressing 120 may be adhered to the patient before the strap 140 is closed over the spin nut 222 and secured by the retention mechanism 139. The tube 224 may be placed in one of the tube clips 150a or 150b to form a "J-loop," which may decrease the likelihood of injury to the patient or dislodgement of the catheter due to tension being placed on the extension set 220. To remove the spin nut 222 from the retainer 130, the medical provider may use the tab 146 to release the strap.

In this way, the catheter 210, catheter hub 212, and extension set 220 may be stabilized by the stabilization system 100. In addition, the insertion site of the catheter will be protected and preserved in a sanitary fashion while the catheter is administered. The medical provider can ensure such protection at the time of stabilization of the catheter, and need not leave the inserted catheter unattended to seek a form of protective covering for the insertion site.

Figure 3:
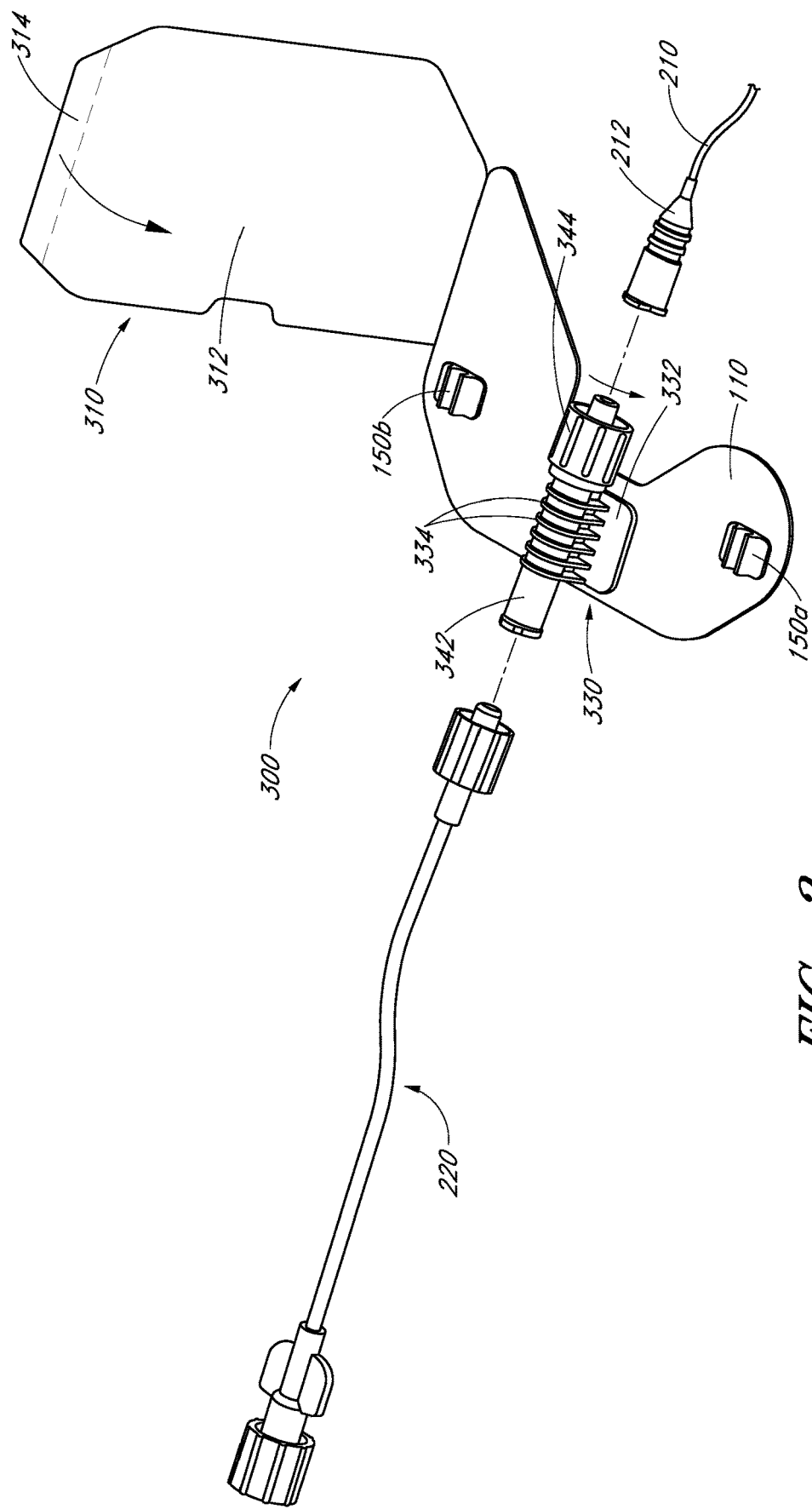
FIG. 3 is a perspective view of another embodiment of a stabilization system and dressing.

With reference now to FIG. 3, an embodiment of a stabilization system 300 includes the anchor pad 110, a dressing 310, tube clips 150a and 150b, and a retainer 330 having an integral connector fitting 342 and spin nut 344. Also shown in FIG. 3 are the catheter 210 attached to the catheter hub 212 and the catheter extension set 220. The anchor pad 110, tube clips 150a and 150b, catheter 210, catheter hub 212, and catheter extension set 220 may all be configured similar to the embodiments described above with respect to FIG. 1.

In the illustrated embodiment, the dressing 310 is covered by a release liner 314. The release liner may be configured similar to the release liner 122 described with respect to FIG. 1. The dressing 310 includes an adhesive surface. In contrast to the adhesive surface 124 described with respect to FIG. 1, the adhesive surface of the dressing 310 is disposed over substantially all of one surface of an occlusive layer of the dressing 310. The dressing 310 may otherwise be configured similar to the dressing 120 described with respect to FIG. 1, and the attachment of the dressing 310 to the anchor pad 110 may be configured similar to the attachment of the dressing 120 to the anchor pad 110. Of course, the adhesive surface may instead be disposed over only a portion of the one surface of the occlusive layer of the dressing 310, for example in any of the ways described above with respect to the adhesive surface 124 and the occlusive layer 126.

The retainer 330 comprises a base 332 attached to and supported by the anchor pad 110. The retainer 330 also comprises the connector fitting 342, which is formed integral to the retainer 330. Annular ribs 334 surround and support the connector fitting 342, and attach the connector fitting 342 to the base 332. In the illustrated embodiment, the annular ribs 334 attach to the base 332 at the sides of the connector fitting 342 such that the attachment location of the annular ribs 334 with the base 332 is slightly laterally offset from the body of the connector fitting 334. The base 332 is shown as being substantially rectangular, but may be any shape that supports the annular ribs 334 and the connector fitting 342.

The spin nut 344 is disposed on the connector fitting 342 such that a catheter hub, such as illustrated by the catheter hub 212, may be connected to the catheter fitting 342. The spin nut 344 is configured with internal threads to engage a portion of the hub 212 and secure the hub to the retainer 330. To accomplish this engagement, the spin nut 344 is configured to rotate about the connector fitting 342.

The connector fitting 342 is configured to attach to a distal medical article for carrying fluids to or from the catheter 210, for example to the catheter extension set 220. The connector fitting 342 may therefore be formed with a lumen extending therethrough along a generally longitudinal axis in order to carry the fluids. In the illustrated embodiment, the connector fitting 342 is configured with a female luer-lock connection fitting to accept the male luer-lock connection fitting disposed on the extension set 220. In some embodiments, the connector fitting 342 comprises a vented one-way valve.

As described above, the annular ribs 334 support and secure the connector fitting 342. Integral securement of the connector fitting 342 in this way increases the stability of the connector fitting 342 with respect to the base 332 and the anchor pad 110. The ribs 334 may increase the ease with which a medical provider may grip the retainer 330. In addition, the spacing between the ribs may be configured such that the ribs 334 may be bent or deflected slightly when pressure is applied by a medical provider. This deflection may increase the ease with which the connector fitting 342 may be manipulated, while decreasing the likelihood of the retainer 330 breaking. Such deflection may similarly provide a shock absorbing effect when pressure is applied to the connector fitting 342, for example by a medical article attached to the connector fitting 342 being pulled or manipulated.

The retainer 330 may comprise materials similar to those described above with respect to the retainer 130. Similarly, the retainer 330 may be formed as a single unit, or may be formed as several different elements and integrated together.

Figure 4:
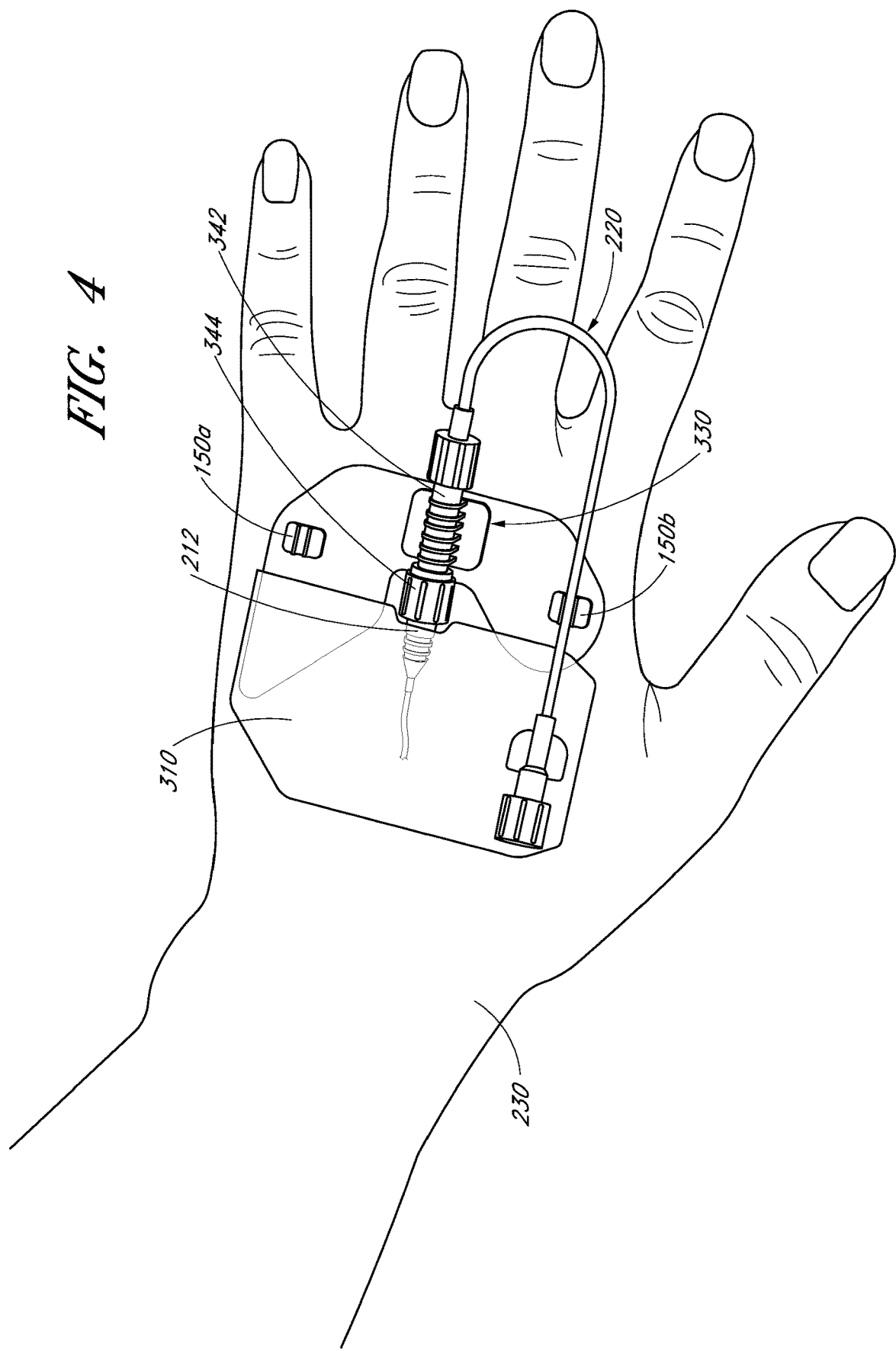
FIG. 4 is a top view of the stabilization system of FIG. 3 secured to a patient with the dressing folded against the patient.

FIG. 4 illustrates the stabilization system 300 secured to the hand 230 of the patient. Those of skill in the art, however, will recognize that the stabilization system 300 may instead be secured to other portions of a patient's body. In the illustrated embodiment in FIG. 4, the stabilization system 300 is illustrated in mirror image to the configuration shown in FIG. 3. Those of skill in the art will understand that the relative positioning of various elements of the stabilizing system 300 thus may be altered without compromising the advantages provided by the stabilizing system 300.

The operation of the stabilization system 300 is similar to the operation of the stabilization system 100 described above, except that the connector fitting 342 is already secured in the stabilization system 300. After the catheter 210 is inserted into the hand 230, the hub 212 may be connected to the connector fitting 342 using the spin nut 344. At this time, the anchor pad 110 may be affixed to the hand 230. In some embodiments, the anchor pad 110 will have already been adhered to the hand 230.

During this time, the dressing 310 is held away from the catheter 210 and the insertion site, similar to the way in which the dressing 120 is held away from the insertion site. The release liner 314 of the dressing 310 may then be removed to expose the adhesive surface. The dressing 310 is folded down over the insertion site and adhered to the skin of the patient, as shown in FIG. 4.

At this point, the catheter 210 and catheter hub 212 are secured to and stabilized by the stabilization system 300. However, the medical provider may additionally connect the extension set 220 to the stabilization system 300 by screwing the spin nut onto the connector fitting 342. The tube of the extension set may be placed in one of the tube clips 150a or 150b to form a "J-loop."

Figure 5:
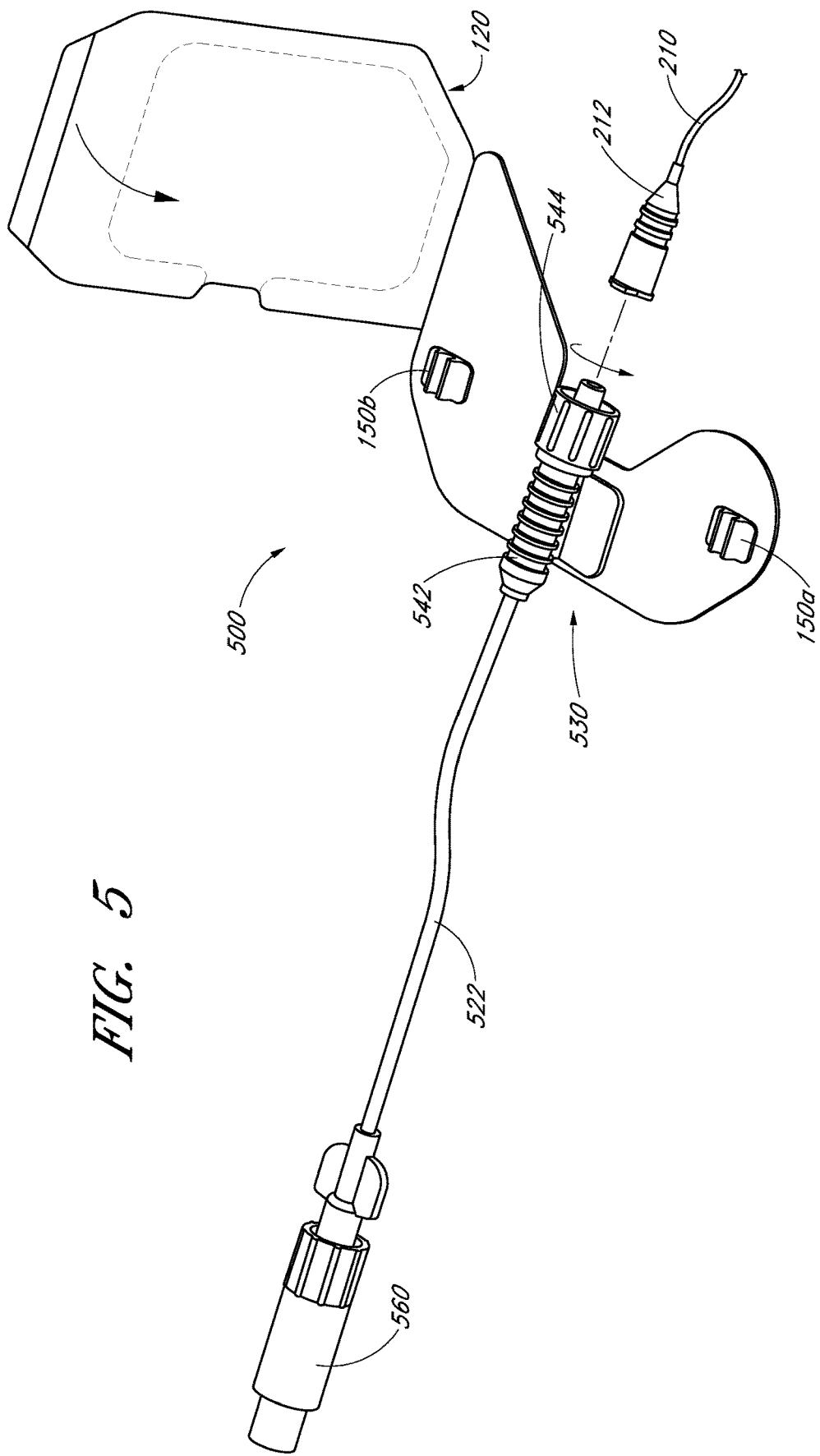
FIG. 5 is a perspective view of another embodiment of a stabilization system and dressing.

With reference now to FIG. 5, an embodiment of a stabilization system 500 includes the anchor pad 110, the dressing 120, tube clips 150a and 150b, and a retainer 530 having an integral connector fitting 542, spin nut 544, and tube 522, and valve 560. Also shown in FIG. 3 is the catheter 210 attached to the catheter hub 212. The anchor pad 110, dressing 120, tube clips 150a and 150b, catheter 210, and catheter hub 212 may all be configured similar to the embodiments described above with respect to FIG. 1.

The stabilization system 500 differs from the stabilization system 300 in that the integrated connector fitting 542 is permanently attached to a tube 522 and valve 560. The stabilization system 300, on the other hand, included an integral connector fitting 342 that was configured to selectively connect to a catheter extension set. The valve 560 may comprise a needleless valve. In some embodiments, a spin nut is attached to the tube 522 instead of the valve 560 being attached. Those of skill in the art will recognize other connectors, fittings, or hubs that may be attached to the tube 522 in place of the valve 560.

The retainer 530 includes a base configured similar to the base 332, except that the base illustrated in FIG. 5 is configured to support the connector fitting 542. The connector fitting 542 is similarly illustrated as being secured and supported by annular ribs. However, the retainer 530 is illustrated as having ribs that connect to the base underneath the connector fitting 542 instead of laterally to the side of the connector fitting 542. Such configuration may allow a greater degree of flexibility of the connector fitting 542 with respect to the base than would be allowed by the stabilization system 300 illustrated in FIG. 3.

Figure 6:
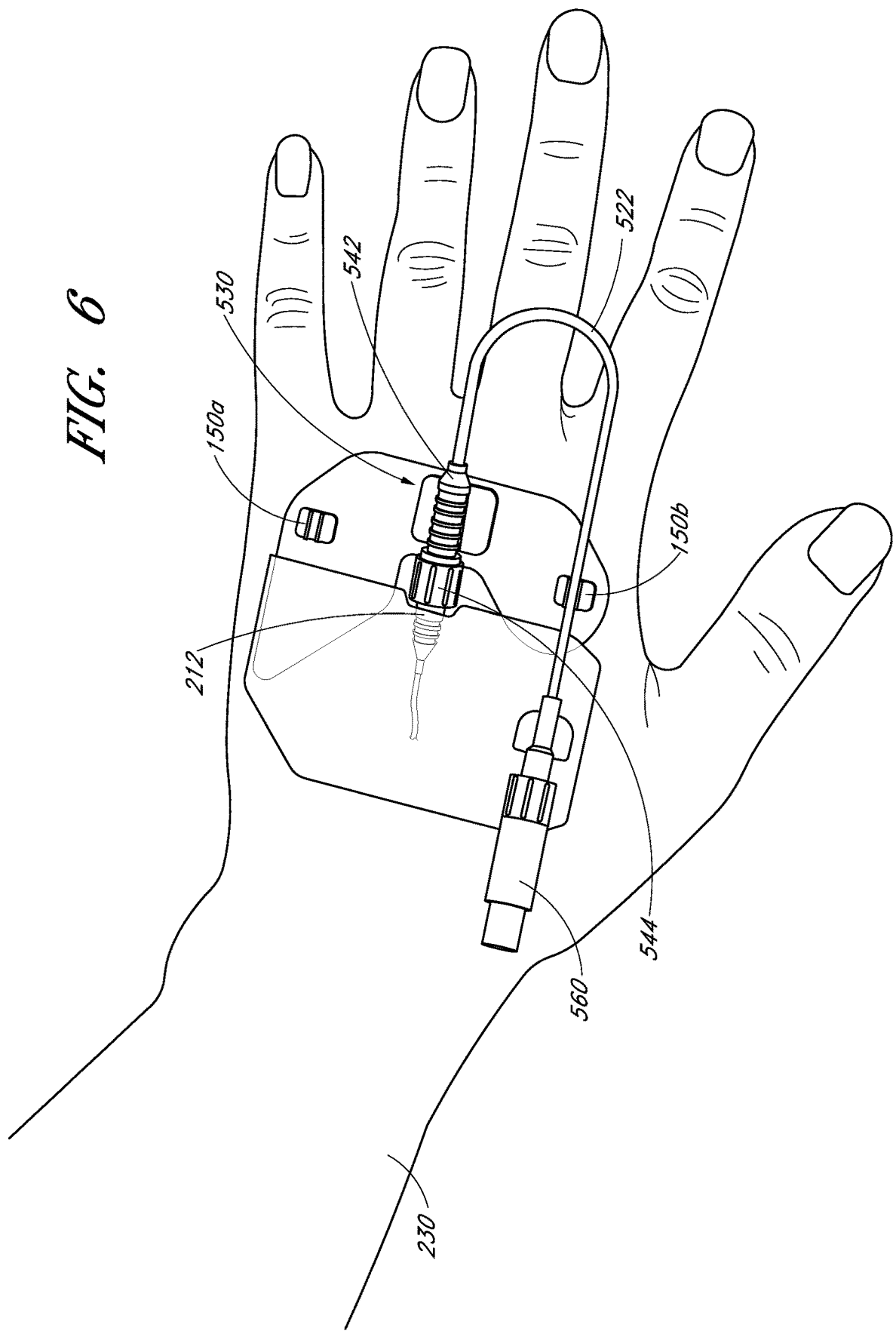
FIG. 6 is a top view of the stabilization system of FIG. 5 secured to the patient with the dressing folded against the patient.

FIG. 6 illustrates the stabilization system 500 secured to the hand 230 of the patient. Those of skill in the art, however, will recognize that the stabilization system 500 may instead be secured to other portions of a patient's body. In the illustrated embodiment in FIG. 6, the stabilization system 500 is illustrated in mirror image to the configuration shown in FIG. 5. Those of skill in the art will understand that the relative positioning of various elements of the stabilizing system 500 thus may be altered without compromising the advantages provided by the stabilizing system 500.

The operation of the stabilization system 500 is similar to the operation of the stabilization system 300 described above, except that the tube 522 and the valve 560 are already connected to the stabilization system 300. After the catheter 210 is inserted into the hand 230, the hub 212 may be connected to the connector fitting 542 using the spin nut 544. At this time, the anchor pad 110 may be affixed to the hand 230. In some embodiments, the anchor pad 110 will have already been adhered to the hand 230.

During this time, the dressing 120 is held away from the catheter 210 and the insertion site, as described above. The release liner 122 of the dressing 120 may then be removed to expose the adhesive surface 124. The dressing 120 is folded down over the insertion site and adhered to the skin of the patient, as shown in FIG. 6.

At this point, the catheter 210, catheter hub 212, tube 522, and valve 560 are all secured to the stabilization system 300, and the connector fitting 542 is stabilized on the patient. The medical provider may then introduce fluids or medicaments into the catheter 210 for administration to the patient through the valve 560. The tube 522 of the extension set may be placed in one of the tube clips 150a or 150b to form a "J-loop."

Figure 7:
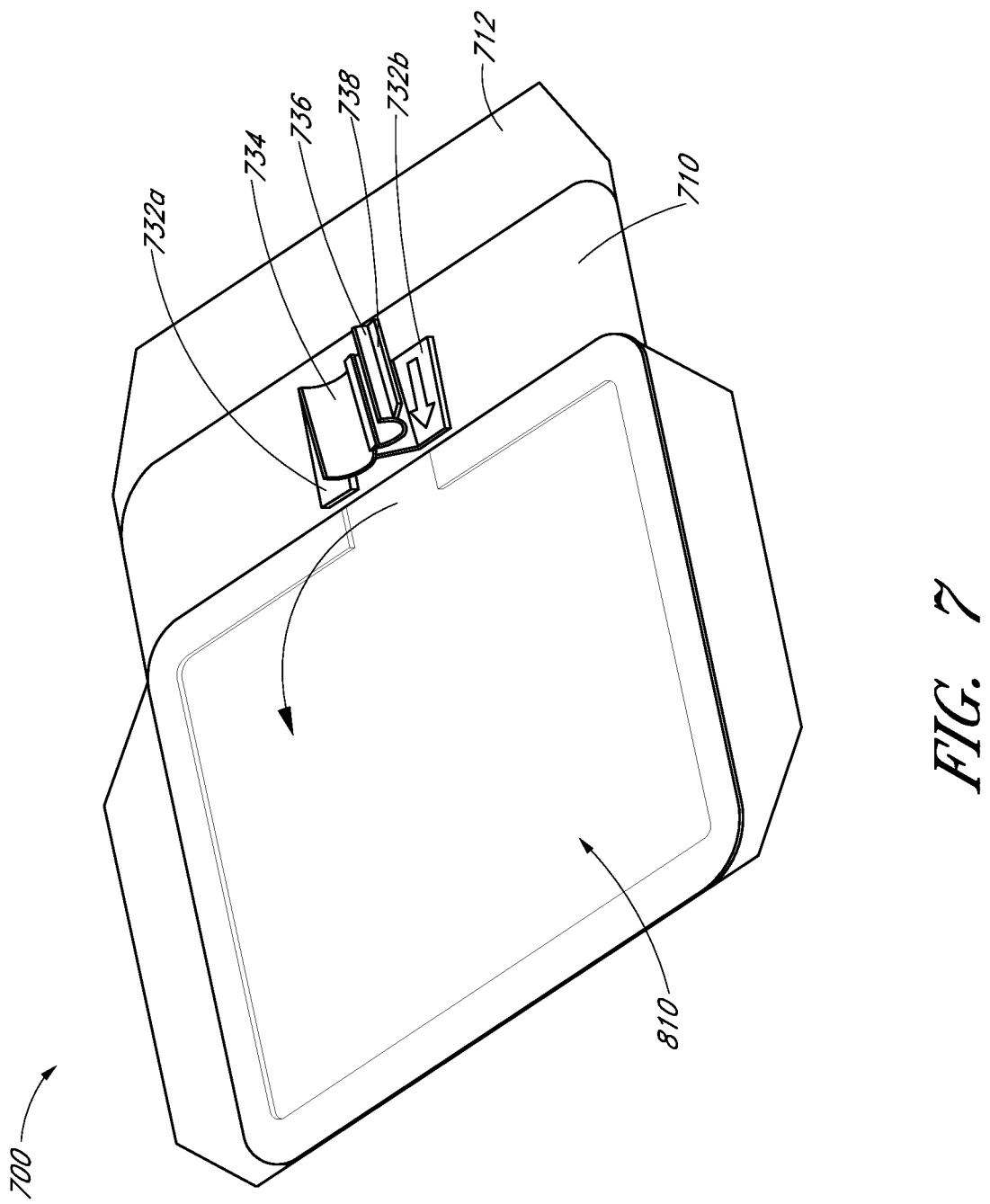
FIG. 7 is a perspective view of another embodiment of a stabilization system and dressing, and shows a retainer in an open position.

With reference now to FIG. 7, an embodiment of a stabilization system 700 includes an anchor pad 710, a dressing 810 integrated with the anchor pad 710, and a retainer 730. In the illustrated embodiment, the dressing 810 is shown as being folded down over the anchor pad 710, but those of skill in the art will understand that the dressing 810 may be held in a position away from the anchor pad 710, for example similar to the way in which the dressing 120 is held away from the anchor pad 110, as described above with respect to FIG. 1.

The retainer 730 comprises wings 732a and 732b. The wings 732a and 732b are disposed on either side of and support a fixed channel portion 734. In the illustrated embodiment, the wings 732a and 732b include arrows that point towards an insertion site where a catheter or other medical device stabilized in connection with the stabilization system 700 is inserted into the body of a patient. In other embodiments, the arrows are omitted.

The fixed channel portion 734 is configured to accept at least a portion of a medical article. The fixed channel portion may be configured in a variety of shapes and sizes, similar to the open channel 134 described above with respect to FIG. 1. In the illustrated embodiment, the fixed channel portion 734 is shown as having a substantially semi-circular shape and as having a smooth inner surface.

The retainer 730 also comprises a movable channel portion 736. The moveable channel portion 736 is configured to close over the fixed channel portion 734 to define an enclosed channel therebetween. When a medical article is inserted in the fixed channel portion 734 and the moveable channel portion 736 is closed about the medical article, the medical article will be encircled by the two channel portions. In the illustrated embodiment, the moveable channel portion 736 is configured as having a substantially semi-circular shape. Those of skill in the art will appreciate that other shapes may be utilized.

The movable channel portion 736 may be integral with the fixed channel portion 734, or may be attached thereto. In one embodiment, the movable channel portion 736 is integral to the fixed channel portion 734 and attached by a living hinge. In another embodiment, the moveable channel portion 736 is formed separate from the fixed channel portion 734 and attached thereto, for example by sonic welding. A multitude of attachment means may be used to attach the movable channel portion 736 such that the movable channel portion 736 may be closed over the fixed channel portion 734.

One or both of the fixed channel portion 734 and the moveable channel portion 736 comprise a mechanism configured to engage the other channel portion and maintain the moveable channel portion 736 in a closed position. For example, an interlocking latch mechanism, hook and loop fasteners, or a lip that engages a protrusion or groove may be used to maintain the moveable channel portion 736 in the closed position. Those of skill in the art will recognize other engaging means to maintain the moveable channel portion 736 in a closed position.

A finger tab 738 extends from an outer surface of the moveable channel portion 736. The finger tab 738 provides an area for a medical provider to grasp while manipulating the moveable channel portion 736. In addition, the finger tab 738 may be used to disengage the engaging means when it is desirable to release the moveable channel portion 736 from a closed position.

The retainer 730 may be constructed as a single piece or from a plurality of different pieces. For example, the entire retainer 730 may be formed by injection molding, or the wings 732a, 732b may be formed separately from the fixed channel portion 734 and thereafter joined to form the retainer 730. The retainer 730 or portions thereof may be rigid or flexible. Suitable materials may include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. In one embodiment, the retainer 730 is formed by injection molding using a polyethylene or a polypropylene material or nylon. However, other materials can be utilized.

Figure 8:
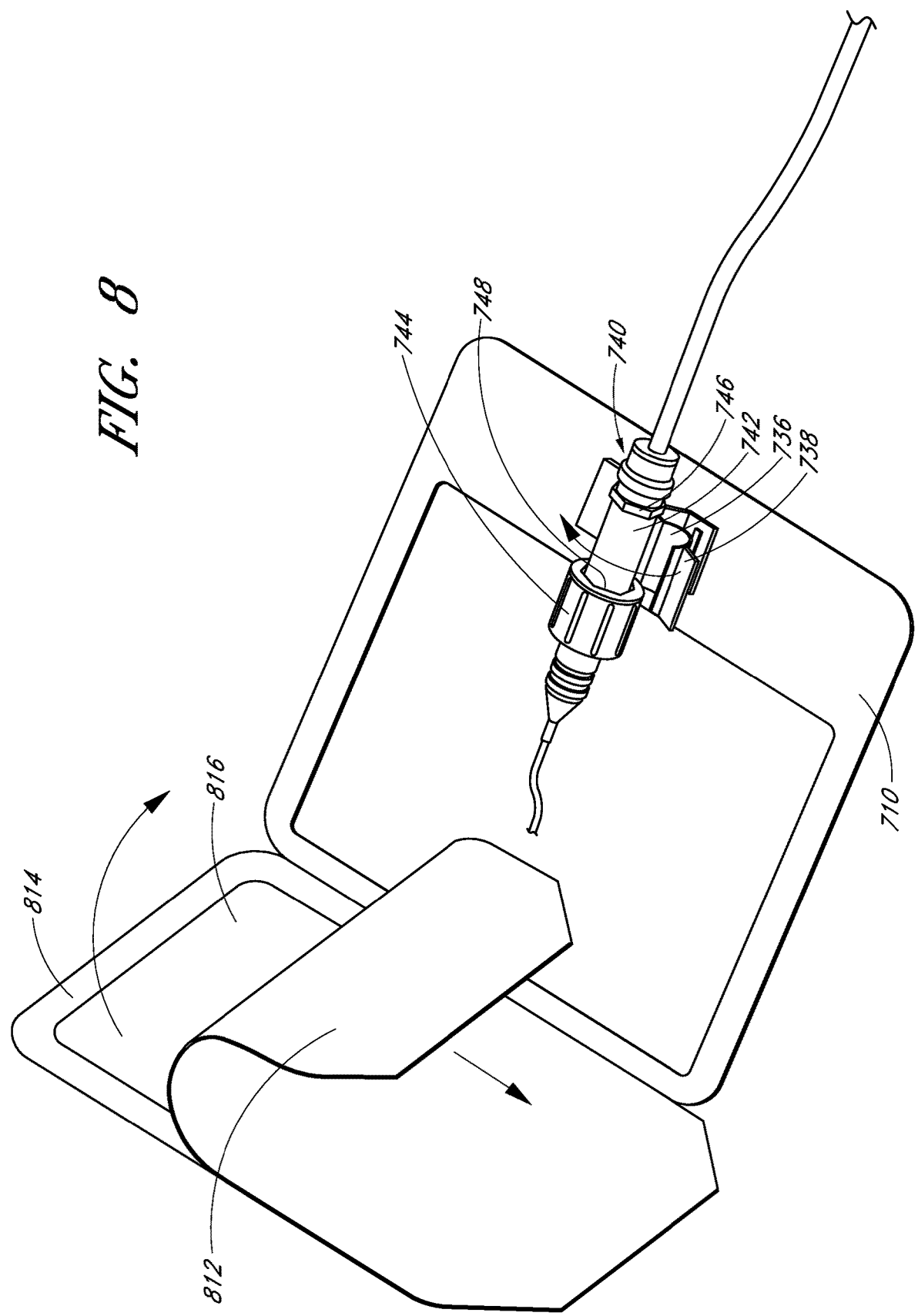
FIG. 8 is another perspective view of the stabilization system of FIG. 7, and shows a medical article placed in the open retainer.

As can be seen in FIG. 8, the dressing 810 may be rotated away from the anchor pad 710 to expose an insertion site area defined and encircled by portion of the anchor pad 710. In the illustrated embodiment, the anchor pad 710 is configured to define a substantially square-shaped insertion site. In other embodiments, the anchor pad defines a circular or elliptical insertion site area or an insertion site area of another shape.

The anchor pad 710 may comprise a lower adhesive surface and an upper layer configured to support the retainer 730. In some embodiments, a release liner covers the lower adhesive surface prior to application of the stabilization system 700. The lower adhesive surface, upper layer, and/or release liner of the anchor pad 710 may be configured similar to the lower adhesive surface, upper layer, and release liner described above with respect to the anchor pad 110. In the embodiment illustrated in FIG. 7, however, the anchor pad is shaped to define an enclosed insertion site area, as described above. In some embodiments, the anchor pad 710 comprises a rigid material or be formed with a rigid layer that maintains the shape of the anchor pad. In some embodiments, the anchor pad 710 is flexible. In some such embodiments, the flexibility of the anchor pad 710 allows a medical provider to vary the size of shape of the insertion site area defined by the anchor pad 710 when applying the anchor pad 710. In some embodiments, a release liner maintains the shape of the anchor pad 710 prior to securing the stabilization system 700 to a patient.

A release liner 812 is disposed on the dressing 810 and covers an adhesive layer 814. The release liner 812 may be configured similar to the release liner 122 described with respect to FIG. 1, and the adhesive layer 814 may be configured similar to the adhesive layer 124. In the illustrated embodiment, the adhesive surface 814 is formed as a ring on the periphery of an occlusive layer 816, which may be configured similar to the occlusive layer 126. A gap or interruption may be formed in the ring of adhesive such that a medical article secured by the stabilization system 700 will not be contacted by the adhesive. In some embodiments, the adhesive surface 814 is disposed over a greater area of the occlusive layer 816, for example similar to the disposition of the adhesive surface on the dressing 310 described above with respect to FIG. 3. In some embodiments, the occlusive layer 816 comprises a notch, for example similar to the notch 128 described above with respect to FIG. 1.

The dressing 810 is attached to or integrated with the anchor pad 710, similar to the way that the dressing 120 is attached to the anchor pad 110. As can be seen in FIG. 8, however, the dressing is attached to the anchor pad 710 along a proximal edge of the anchor pad 710 such that the dressing 810 will be folded longitudinally towards the retainer 730 to cover at least a portion of the insertion site area. In the illustrated embodiment, the dressing 810 is secured to an edge of the anchor pad 710 that is generally parallel to a lateral axis. The dressing 810, however, may be attached to or integrated with the anchor pad 710 such that the dressing 810 is skewed with respect to a longitudinal and/or a lateral axis. In the illustrated embodiment, the dressing 810 is configured to cover the entire insertion site area defined by the anchor pad 710 when folded down or closed.

In the illustrated embodiment, the stabilization system 700 is configured to stabilize a connector fitting 740. The connector fitting 740 comprises an elongated body 742 and a spin nut 744. The spin nut 744 is desirably disposed such that the central axis of the spin nut 744 is generally the same as the central axis of the elongated body 742 of the connector fitting 740. The spin nut 744 may be free to rotate about and slide along the axis of the connector fitting 740.

The spin nut 744 desirably has an internal screw thread disposed upon the inner surface of the spin nut 744. This screw thread will engage with a screw thread of the catheter hub 212 when the hub 212 is secured to the connector fitting 740. A distal wall of the spin nut 744 is visible in FIG. 8. This wall forms a distal end of the spin nut 744. In the illustrated embodiment, a receptacle 748 is formed in the distal wall of the spin nut 744.

As illustrated in FIG. 8, the spin nut 744 is disposed in a proximal position. However, when the spin nut 744 is in a distal position, the receptacle 748 receives at least a portion of an outwardly extending member 746. When the spin nut 744 is in the fully distal position, the member 746 is inserted into the receptacle 748.

The receptacle 748 has a cross-sectional shape which substantially approximates the shape of the member 746. In this embodiment, the member is hexagonally shaped, but other shapes may be used. When the receptacle 748 is placed about the member 746, a twisting motion applied to the spin nut 744 will be transferred to the connector fitting 740, allowing the spin nut 50 to be gripped when attempting to remove the connector fitting 740 from the hub 212.

In addition to providing a mechanism for the transfer of torque between the spin nut 744 and the connector fitting 740, the receptacle 748 also is capable of exerting a distally directed axial force upon the member 742 due to a lip formed inside the spin nut 744 or due to the distal surface of the spin nut 744 abutting the circular annular ring illustrated distal to the member 746. This interaction between the proximal surface the annular ring also inhibits migration of the spin nut 744 distally off of the end of the connector fitting 740. This maintains the spin nut 744 upon the connector fitting 740, eliminating the need for medical personnel to locate a spin nut which may have moved off of the fitting 740. This allows for more rapid and reliable release of the connector fitting 740 from the catheter hub 212. An annular ring or other stop member may also be disposed near a proximal end of the elongated body 742 to prevent migration of the spin nut 744 off of a proximal end of the elongated body 742. In such embodiment, the proximal annular ring or stop member may be sized and/or shaped to allow the spin nut 744 to advance partially over the ring or stop up until a point where the proximal side of the distal wall of the spin nut 744 contacts or abuts the ring or stop.

As can be seen in FIG. 8, the channel portions 734 and 736 are configured to accept the connector fitting 740. Thus, when the moveable channel portion 736 is closed about the connector fitting 740, the body member 742 will be tightly encircled. Abutment of the distal surface against the channel portions 734 and 736 will inhibit longitudinal motion of the catheter fitting 740 within the retainer 730, as will abutment of the peripherally extending member 746 or the distal annular ring against the channel portions 734 and 736. In some embodiments, the length of the fixed channel portion 734 and/or the movable channel portion 736 is approximately equivalent to the length of the portion of the elongated body 742 disposed between the distal wall of the spin nut 744 when the spin nut 744 is fully advanced in the proximal direction and the peripherally extending member 746. In this configuration, longitudinal motion of the catheter fitting 740 in either direction will be inhibited. The channel portions 734 and 736 will also inhibit transverse motion of the connector fitting 740 within the retainer 730, and may further inhibit lateral motion of the connector fitting 740 or rotation or the connector fitting 740 in at least a plane parallel to or transverse to the anchor pad 710.

As shown in FIG. 8, after the catheter 210 is inserted into the hand 230 and the hub 212 connected to the connector fitting 740 by using the spin nut 744, the connector fitting 740 is placed in the fixed channel portion 734 of the retainer 730. Preferably, the anchor pad 710 will have already been adhered to the hand 230 about the insertion site. Alternatively, a slit may be provided or cut in the anchor pad 710 to allow the anchor pad to be placed around the catheter 210. During this time, the dressing 810 is held away from the catheter 210 and the insertion site, which may be accomplished similar to the ways described above with respect to the dressing 120 and the anchor pad 110 illustrated in FIG. 1.

Figure 9:
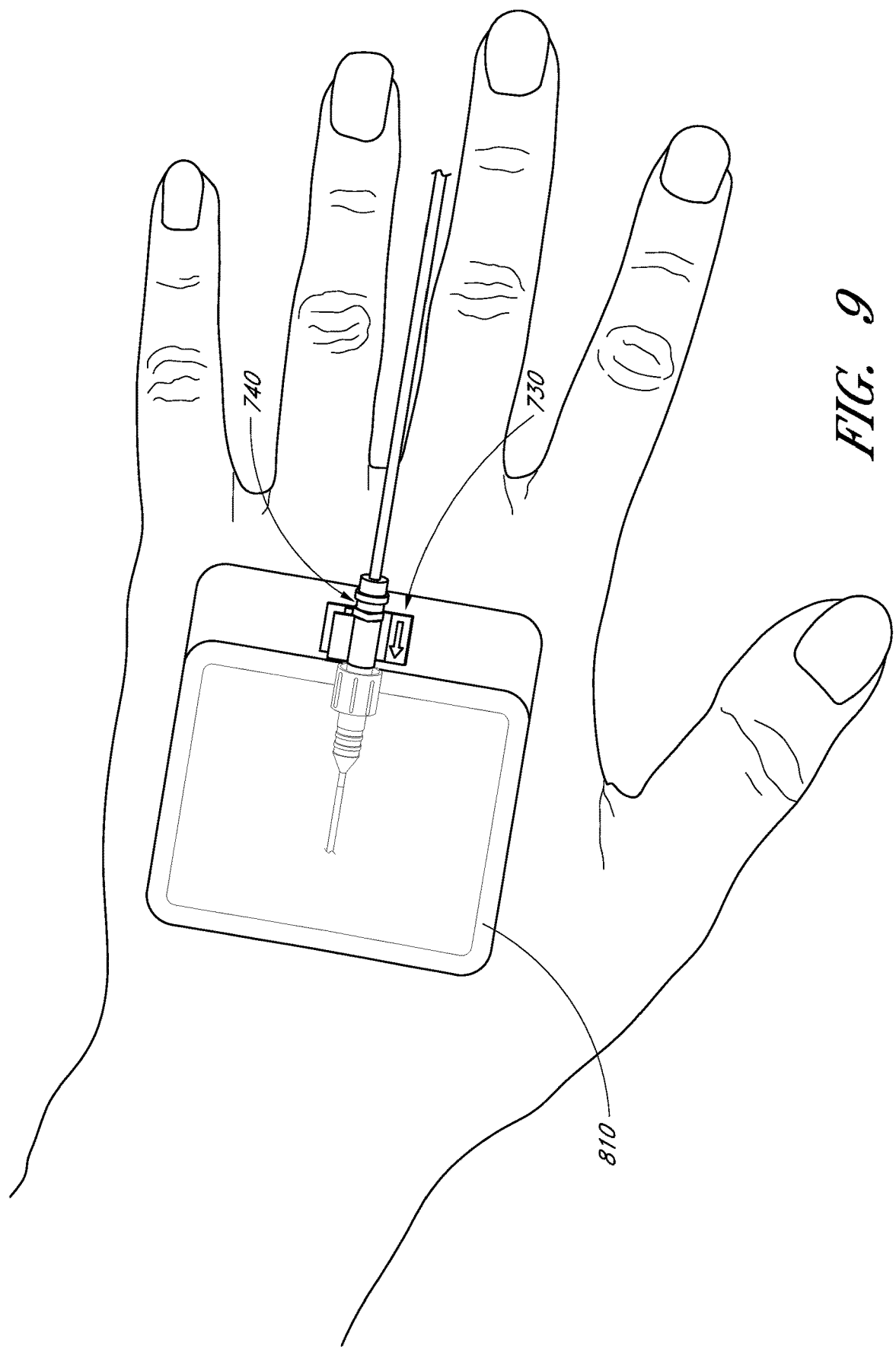
FIG. 9 is a top view of the stabilization system of FIG. 7 secured to a patient with the dressing folded against the patient with the retainer in the closed position.

The moveable channel portion 736 is then placed over the connector fitting 740 until the moveable channel portion 736 engages the fixed channel portion 734. At this time, the release liner 812 of the dressing is removed to expose the adhesive surface 814. The dressing 810 is folded down over the insertion site and adhered to the skin of the patient, as shown in FIG. 9. Of course, the dressing 810 may be adhered to the patient before the moveable channel portion 736 is closed over the connector fitting 740 and secured to the fixed channel portion 734. A medical provider may manipulate the moveable channel portion 736 using the finger tab 738, and similar may utilize the finger tab 738 to release the moveable channel portion 736 form the fixed channel portion 734 in order to thereafter remove the connector fitting 740 from the retainer 730.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a stabilization system, and stabilization systems that include one or more of the features herein described can be designed for use with a variety of medical articles.

The various embodiments of the stabilization systems described above in accordance with the present invention thus provide a means to releasably secure a connector fitting or extension set to a patient. An insertion site of a catheter attached to the connector fitting or extension set may be covered with an integrated dressing.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct stabilization systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but by a fair reading of the claims that follow.

What is claimed is:

1. A stabilization system comprising:
    an anchor pad having a surface, at least a portion of the surface being covered by an adhesive for attachment to a patient's skin;
    a connector fitting supported by the anchor pad and having a spin nut, the spin nut being configured to secure to a catheter hub; and
    a dressing secured to the anchor pad so as to move between an open position and a closed position, the connector fitting left uncovered by the dressing in the closed position.

2. The stabilization system of claim 1, further comprising a plurality of ribs encircling at least a portion of the connector fitting.

3. The stabilization system of claim 2, wherein the plurality of ribs are configured to flex in at least a longitudinal direction when pressure is applied to the connector fitting.

4. The stabilization system of claim 2, further comprising a base disposed between the connector fitting and the anchor pad, wherein one or more of the ribs are connected to a portion of the base, and wherein the base is laterally offset from the connector fitting.

5. The stabilization system of claim 2, further comprising a base disposed between the connector fitting and the anchor pad, wherein one or more of the ribs are connected to a portion of the base that is aligned with the connector fitting, and wherein the one or more of the ribs and the base are connected along a transverse axis.

6. The stabilization system of claim 1, wherein the connector fitting comprises a one-way valve.

7. The stabilization system of claim 1, wherein the dressing folds down over at least a portion of the anchor pad.

8. The stabilization system of claim 7, wherein the dressing includes an indent to receive at least a portion of the connector fitting in the closed position.

9. The stabilization system of claim 8, wherein the dressing comprises an adhesive disposed in a discontinuous ring about a periphery of the dressing, a discontinuity in the discontinuous ring positioned at the indent.

10. A stabilization system comprising:
    an anchor pad having a surface, at least a portion of the surface being covered by an adhesive for attachment to a patient's skin;
    an extension set supported by the anchor pad and having a spin nut, the spin nut being configured to secure to a catheter hub;
    a tube clip configured to retain a portion of the extension set; and
    a dressing secured to the anchor pad so as to move between an open position and a closed position, the tube clip left uncovered by the dressing in the closed position.

11. The stabilization system of claim 10, wherein the dressing comprises an adhesive configured for attachment to the patient's skin.

12. The stabilization system of claim 11, wherein the adhesive of the dressing is disposed in a ring about a periphery of the dressing.

13. The stabilization system of claim 12, wherein the ring is discontinuous.

14. The stabilization system of claim 10, wherein the extension set comprises a needleless valve.

15. The stabilization system of claim 10, wherein the extension set is permanently secured to a tube.

\* \* \* \* \*